United States Patent
Cassayre et al.

(10) Patent No.: US 10,266,524 B2
(45) Date of Patent: Apr. 23, 2019

(54) PROCESS FOR THE PREPARATION OF THIETANE DERIVATIVES

(71) Applicants: Jerome Yves Cassayre, Stein (CH); Peter Renold, Stein (CH); Thomas Pitterna, Stein (CH); Myriem El Qacemi, Stein (CH)

(72) Inventors: Jerome Yves Cassayre, Stein (CH); Peter Renold, Stein (CH); Thomas Pitterna, Stein (CH); Myriem El Qacemi, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/596,766

(22) Filed: May 16, 2017

(65) Prior Publication Data
US 2017/0247361 A1    Aug. 31, 2017

Related U.S. Application Data

(62) Division of application No. 14/931,315, filed on Nov. 3, 2015, now Pat. No. 9,682,949, which is a division of application No. 14/240,541, filed as application No. PCT/EP2012/066552 on Aug. 24, 2012, now Pat. No. 9,204,648.

(30) Foreign Application Priority Data

Aug. 25, 2011    (EP) .................................. 11178929

(51) Int. Cl.
| | | |
|---|---|---|
| *C07D 413/12* | (2006.01) | |
| *A01N 43/36* | (2006.01) | |
| *A01N 43/80* | (2006.01) | |
| *C07D 331/04* | (2006.01) | |
| *C07D 409/12* | (2006.01) | |

(52) U.S. Cl.
CPC ........... *C07D 413/12* (2013.01); *A01N 43/36* (2013.01); *A01N 43/80* (2013.01); *C07D 331/04* (2013.01); *C07D 409/12* (2013.01)

(58) Field of Classification Search
CPC ................................................... C07D 413/12
See application file for complete search history.

(56) References Cited

FOREIGN PATENT DOCUMENTS

| WO | 2009080250 | 7/2009 |
|---|---|---|
| WO | 2010020521 | 2/2010 |
| WO | 2011054871 | 5/2011 |
| WO | 2011104087 | 9/2011 |
| WO | 2011104088 | 9/2011 |
| WO | 2011154555 A1 | 12/2011 |
| WO | 2012104331 A2 | 8/2012 |

OTHER PUBLICATIONS

Qacemi, et al. Document No. 156:74224, retrieved from STN; WO 2011154555; Dec. 15, 2011.
International Search Report dated Oct. 25, 2012 International Patent Application No. PCT/EP2012/066552.
Burkhard, J.A., "Synthesis and Structural Analysis of a New Class of Azaspiro[3.3] heptanes as Building Blocks for Medicinal Chemistry," Organic Letters, 12(9), May 7, 2010, p. 1944-1947.
Seitz, G. et al., "Heteroanalogs of methylenecyclobutane and bicyclobutylidene," Chemiker Zeitung, Wiley-VCH Verlag GmBH & Co. KGAA, DE, 100(10), Jan. 1, 1976, p. 440.
Burkhard, J.A., "Synthesis and Structural Analysis of a New Class of Azaspiro[3.3] hepatanes as Building Blocks for Medicinal Chemistry," Organic Letters, 12(9), May 7, 2010, p. 1944-1947.
Seitz, G. et al., "Heteroanalogs of methylenecyclobutane and bicyclobutylidine," Chemiker Zeitung, Wiley-VCH Verlag GmBH & Co. KGAA, DE, 100(10), Jan. 1, 1976, p. 440.

*Primary Examiner* — Shawquia Jackson
(74) *Attorney, Agent, or Firm* — Dinsmore & Shohl LLP; Toni-Junell Herbert

(57) ABSTRACT

The present invention relates to processes for the preparation of thietane derivatives of the formula IA

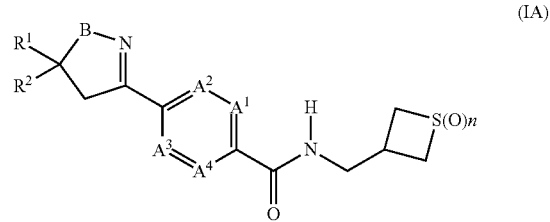

(IA)

and thietane derivatives of the formula IB

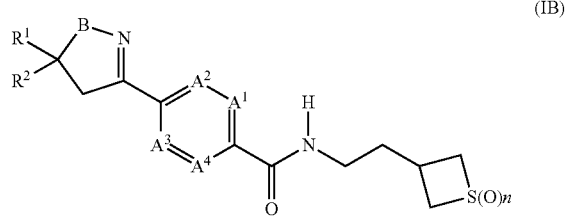

(IB)

wherein $R^1$, $R^2$, $A^1$, $A^2$, $A^3$, $A^4$, B, and n are as defined in the claims. The invention also relates to intermediates useful in the processes, as well as the compounds of formula IA and IB and their use as pesticides.

3 Claims, No Drawings

PROCESS FOR THE PREPARATION OF THIETANE DERIVATIVES

RELATED APPLICATION INFORMATION

This application is a divisional of U.S. patent application Ser. No. 14/931,315 filed Nov. 3, 2015, which is a divisional of U.S. patent application Ser. No. 14/240,541 filed 24 Feb. 2014 which was a 371 of International Application No. PCT/EP2012/066552, filed 24 Aug. 2012, which claims priority to EP Patent Application No. 11178929.3, filed 25 Aug. 2011, the contents of which are incorporated herein by reference herein.

The present invention relates to processes for the preparation of novel insecticidally active thietane derivatives. The invention also relates to the thietane derivatives and to intermediates used in the preparation of the thietane derivatives, as well as methods of using the thietane derivatives to combat and control insect, acarine, nematode and mollusc pests.

Certain thietane derivatives with insecticidal properties are disclosed, for example, in WO2009/080250.

New procedures for synthesising insecticidally active thietane derivatives having an alkylene group between the thietane and amide groups have now surprisingly been discovered, allowing easier and potentially cheaper access to these compounds, and thereby opening up the possibility of commercial production.

In a first aspect the invention provides a process for the preparation of a compound of formula IA

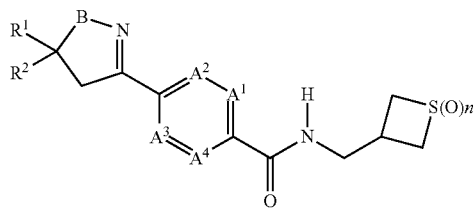
(IA)

wherein
$A^1, A^2, A^3$ and $A^4$ are independently of one another C—H, C—$R^3$, or nitrogen;
B is O or $CH_2$;
$R^1$ is $C_1$-$C_8$haloalkyl;
$R^2$ is aryl or aryl substituted by one to five $R^4$, or heteroaryl or heteroaryl substituted by one to five $R^4$;
each $R^3$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, amino, hydroxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or two $R^3$ on adjacent carbon atoms together form a —CH=CH—CH=CH— bridge or a —N=CH—CH=CH— bridge;
each $R^4$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^5$, or heterocyclyl or heterocyclyl substituted by one to five $R^5$;
each $R^5$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;
n is 0, 1 or 2;
comprising preparing a compound of formula IV

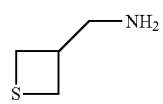
(IV)

By either
a. reacting a compound of formula II

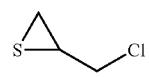
(II)

with a source of cyanide in the presence of water to give a compound of formula III

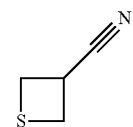
(III)

b. reducing the compound of formula III with a suitable reducing agent to give a compound of formula IV

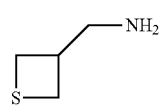
(IV)

c-i. reacting the compound of formula IV with a compound of formula V

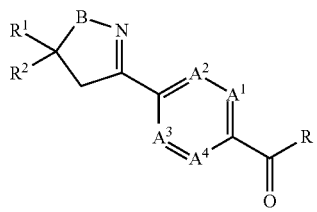
(V)

wherein R is OH, $C_1$-$C_6$alkoxy or Cl, F or Br, and $R^1$, $R^2$, B, $A^1$, $A^2$, $A^3$ and $A^4$ are as defined for compounds of formula IA to give a compound of formula I; or A) reacting a compound of formula VII

(VII)

with $CH_3NO_2$ to give a compound of formula XI

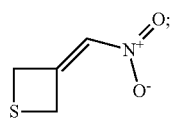
(XI)

B) reducing the compound of formula XI with a suitable reducing agent to give a compound of formula IV; or 1) homologating a compound of formula VII

(VII)

to give an ester of formula XII

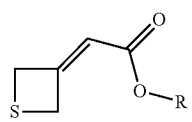
(XII)

wherein R is $C_1$-$C_6$alkyl;

2) reducing the compound of formula XII using a suitable reducing agent to give a compound of formula XIII

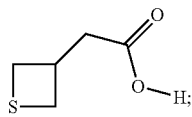
(XIII)

3) treating the compound of formula XIII with hydrazoic acid to give a compound of formula IV; and c-i. reacting the compound of formula IV with a compound of formula V

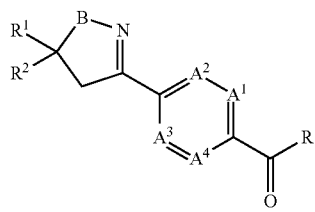
(V)

wherein R is OH, $C_1$-$C_6$alkoxy or Cl, F or Br, and $R^1$, $R^2$, B, $A^1$, $A^2$, $A^3$ and $A^4$ are as defined for compounds of formula I to give a compound of formula IA; or c-ii reacting the compound of formula IV with a compound of formula VI

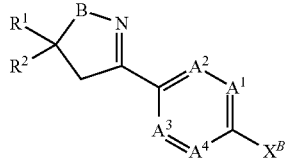
(VI)

wherein $X^B$ is a leaving group for example a halogen, such as bromo, and $R^1$, $R^2$, B, $A^1$, $A^2$, $A^3$ and $A^4$ are as defined for compounds of formula IA with carbon monoxide in the presence of a suitable catalyst to give a compound of formula IA;

and wherein the method optionally comprises oxidizing the sulfur atom of the thietane moiety.

The source of cyanide in step a. is for example $CN^-$, e.g. provided as a cyanide salt such as a alkali metal salt M-CN, wherein M is for example potassium or sodium. In step b. a suitable reducing agent is for example a hydride reagent such as lithium aluminium hydride.

In a further aspect, the invention provides a method of preparing a compound of formula IV

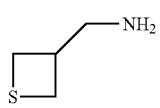
(IV)

comprising a. reacting a compound of formula II

(II)

with a source of cyanide in the presence of water to give a compound of formula III

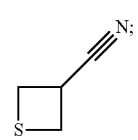
(III)

b. reducing the compound of formula III with a suitable reducing agent to give a compound of formula IV.

In a further aspect, the invention provides a method of preparing a compound of formula IV

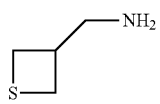
(IV)

comprising

A) reacting a compound of formula VII

(VII)

with CH$_3$NO$_2$ to give a compound of formula XI

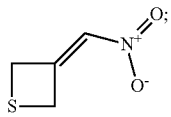
(XI)

B) reducing the compound of formula XI with a suitable reducing agent to give a compound of formula IV.

In a further aspect, the invention provides a method of preparing a compound of formula IV

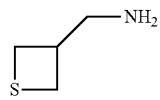
(IV)

comprising
1) homologating a compound of formula VII

(VII)

to give an ester of formula XII

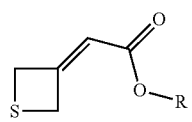
(XII)

wherein R is C$_1$-C$_6$alkyl;
2) reducing the compound of formula XII using a suitable reducing agent to give a compound of formula XIII

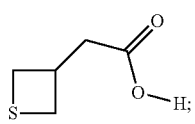
(XIII)

3) treating the compound of formula XIII with hydrazoic acid to give a compound of formula IV.

In a further aspect the invention provides a compound of formula IA

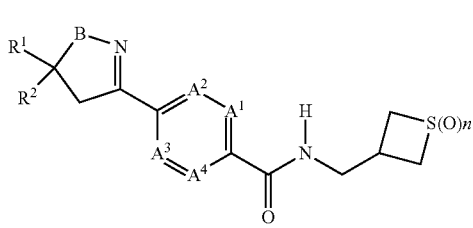
(IA)

wherein
A$^1$, A$^2$, A$^3$ and A$^4$ are independently of one another C—H, C—R$^3$, or nitrogen;
B is O or CH$_2$;
R$^1$ is C$_1$-C$_8$haloalkyl;
R$^2$ is aryl or aryl substituted by one to five R$^4$, or heteroaryl or heteroaryl substituted by one to five R$^4$;
each R$^3$ is independently halogen, cyano, nitro, C$_1$-C$_8$alkyl, C$_3$-C$_8$cycloalkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, C$_1$-C$_8$alkoxy, C$_1$-C$_8$haloalkoxy, C$_1$-C$_8$alkoxycarbonyl-, amino, hydroxy, mercapto, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl, C$_1$-C$_8$haloalkylsulfonyl, C$_1$-C$_8$alkylcarbonyl, or two R$^3$ on adjacent carbon atoms together form a —CH═CH—CH═CH— bridge or a —N═CH—CH═CH— bridge;
each R$^4$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, hydroxy, C$_1$-C$_8$alkoxy, C$_1$-C$_8$haloalkoxy, mercapto, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl, C$_1$-C$_8$haloalkylsulfonyl, C$_1$-C$_8$alkylcarbonyl, C$_1$-C$_8$alkoxycarbonyl, aryl or aryl substituted by one to five R$^5$, or heterocyclyl or heterocyclyl substituted by one to five R$^5$;
each R$^5$ is independently halogen, cyano, nitro, C$_1$-C$_4$alkyl, C$_1$-C$_4$haloalkyl, C$_1$-C$_4$alkoxy-, or C$_1$-C$_4$haloalkoxy-.

In a further aspect the invention provides a process for the preparation of a compound of formula IB,

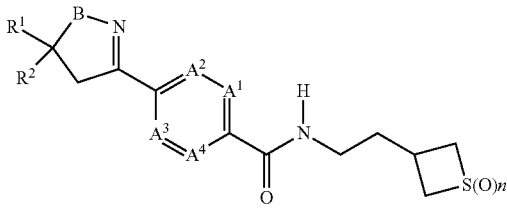
(IB)

wherein
A$^1$, A$^2$, A$^3$ and A$^4$ are independently of one another C—H, C—R$^3$, or nitrogen;
B is O or CH$_2$;
R$^1$ is C$_1$-C$_8$haloalkyl;
R$^2$ is aryl or aryl substituted by one to five R$^4$, or heteroaryl or heteroaryl substituted by one to five R$^4$;
each R$^3$ is independently halogen, cyano, nitro, C$_1$-C$_8$alkyl, C$_3$-C$_8$cycloalkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, C$_1$-C$_8$alkoxy, C$_1$-C$_8$haloalkoxy, C$_1$-C$_8$alkoxycarbonyl-, amino, hydroxy, mercapto, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl, C$_1$-C$_8$haloalkylsulfonyl, C$_1$-C$_8$alkylcarbonyl, or two R$^3$ on adjacent carbon atoms together form a —CH═CH—CH═CH— bridge or a —N═CH—CH═CH— bridge;
each R$^4$ is independently halogen, cyano, nitro, C$_1$-C$_8$alkyl, C$_1$-C$_8$haloalkyl, C$_2$-C$_8$alkenyl, C$_2$-C$_8$haloalkenyl, C$_2$-C$_8$alkynyl, C$_2$-C$_8$haloalkynyl, hydroxy, C$_1$-C$_8$alkoxy, C$_1$-C$_8$haloalkoxy, mercapto, C$_1$-C$_8$alkylthio, C$_1$-C$_8$haloalkylthio, C$_1$-C$_8$alkylsulfinyl, C$_1$-C$_8$haloalkylsulfinyl, C$_1$-C$_8$alkylsulfonyl, C$_1$-C$_8$haloalkylsulfonyl, C$_1$-C$_8$alkylcarbonyl, C$_1$-C$_8$alkoxycarbonyl, aryl or aryl substituted by one to five R$^5$, or heterocyclyl or heterocyclyl substituted by one to five R$^5$;
each R$^5$ is independently halogen, cyano, nitro, C$_1$-C$_4$alkyl, C$_1$-C$_4$haloalkyl, C$_1$-C$_4$alkoxy-, or C$_1$-C$_4$haloalkoxy-;
n is 0, 1 or 2;

comprising
i. reacting a compound of formula VII

 (VII)

with triphenylphosphoranyldiene-acetonitrile or (Cyanomethyl)diethoxyphosphine oxide to give a compound of formula VIII

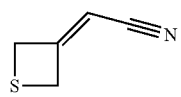 (VIII)

ii. reducing the compound of formula VIII with a suitable reducing agent to give a compound of formula X

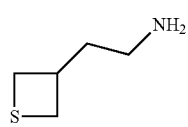 (X)

iii-i. reacting the compound of formula X with a compound of formula V

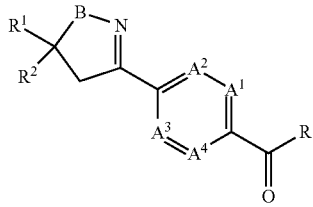 (V)

wherein R is OH, $C_1$-$C_6$alkoxy or Cl, F or Br, and $R^1$, $R^2$, B, $A^1$, $A^2$, $A^3$ and $A^4$ are as defined for compounds of formula I to give a compound of formula IB; or
iii-ii reacting the compound of formula X with a compound of formula VI

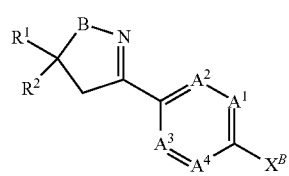 (VI)

wherein $X^B$ is a leaving group for example a halogen, such as bromo, and $R^1$, $R^2$, B, $A^1$, $A^2$, $A^3$ and $A^4$ are as defined for compounds of formula IB with carbon monoxide in the presence of a suitable catalyst to give a compound of formula IB;
and wherein the method optionally comprises oxidizing the sulfur atom of the thietane moiety.

In step ii. a suitable reducing agent is for example a hydride reagent such as a borohydrate, e.g. sodium borohydride, or lithiumaluminium hydride. Step ii may be carried out in two steps, e.g. ii-i, reduction to (thietan-3-yl)acetonitrile e.g. with sodium borohydride, and ii-ii reduction to (thietan-3-yl)ethanamine with lithiumaluminium hydride.

In steps c-i. and iii-i suitable conditions when R is OH are for example diisopropylethylamine (Hunig's Base) and a solution of bis(2-oxo-3-oxazolidinyl)phosphonic chloride ("BOP-Cl"), in the presence of a suitable base. Suitable conditions when R is halogen are for example the presence of a suitable base. Suitable conditions when R is $C_1$-$C_6$alkoxy are for example heating. In steps c-ii and iii-ii a suitable catalyst is for example a catalyst comprising palladium such as palladium(II) acetate or bis(triphenylphosphine)palladium(II) dichloride.

In a further aspect the invention provides a process for preparing a compound of formula X

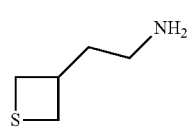 (X)

comprising
i. reacting a compound of formula VII

 (VII)

with triphenylphosphoranyldiene-acetonitrile or (Cyanomethyl)diethoxyphosphine oxide to give a compound of formula VIII

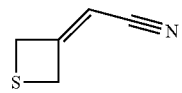 (VIII)

ii. reducing the compound of formula VIII with a suitable reducing agent to give a compound of formula X.

In a further aspect the invention provides a compound of formula IB

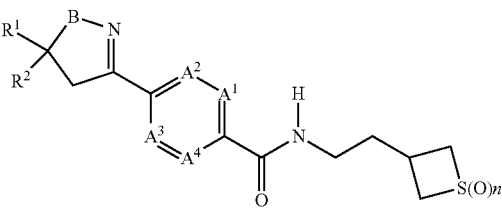 (IB)

wherein
$A^1$, $A^2$, $A^3$ and $A^4$ are independently of one another C—H, C—$R^3$, or nitrogen;
B is O or $CH_2$;

$R^1$ is $C_1$-$C_8$haloalkyl;

$R^2$ is aryl or aryl substituted by one to five $R^4$, or heteroaryl or heteroaryl substituted by one to five $R^4$;

each $R^3$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, amino, hydroxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or two $R^3$ on adjacent carbon atoms together form a —CH=CH—CH=CH— bridge or a —N=CH—CH=CH— bridge;

each $R^4$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^5$, or heterocyclyl or heterocyclyl substituted by one to five $R^5$;

each $R^5$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;

n is 0, 1 or 2.

In a further aspect the invention provides a compound of formula IV or XV

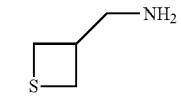

(IV)

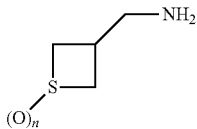

(XIV)

wherein n is 1 or 2.

In a further aspect the invention provides a compound of formula VIII, IX, X or XV

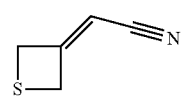

(VIII)

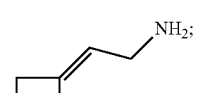

(IX)

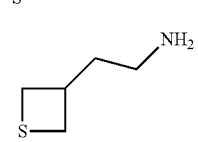

(X)

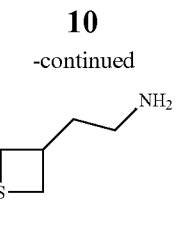

(XV)

In a further aspect the invention provides a compound of formula XI, XII or XIII

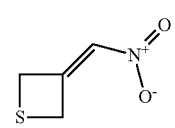

(XI)

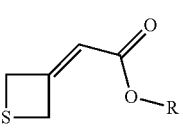

(XII)

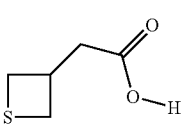

(XIII)

wherein R is $C_1$-$C_6$alkyl.

In a further aspect the invention provides a compound of formula IIIa or

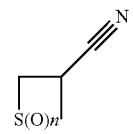

(IIIa)

wherein n is 1 or 2.

The above reaction steps are described in more detail below.

The compounds of formula (I) may exist in different geometric or optical isomers or tautomeric forms. This invention covers all such isomers and tautomers and mixtures thereof in all proportions as well as isotopic forms such as deuterated compounds. The invention also covers salts and N-oxides of all compounds of the invention.

The compounds of the invention may contain one or more asymmetric carbon atoms, for example, in the —$CR^3R^4$— group or at the $LR^2Y^1Y^4$ carbon and may exist as enantiomers (or as pairs of diastereoisomers) or as mixtures of such. Further, where any Y group is SO, the compounds of the invention are sulfoxides, which can also exist in two enantiomeric forms.

Each alkyl moiety either alone or as part of a larger group (such as alkoxy, alkylcarbonyl, or alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$-$C_6$ alkyl groups, more preferably $C_1$-$C_4$ and most preferably $C_1$-$C_3$ alkyl groups.

Alkenyl moieties can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl moieties can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Halogen is fluorine, chlorine, bromine or iodine.

Haloalkyl groups (either alone or as part of a larger group, such as haloalkoxy) are alkyl groups which are substituted by one or more of the same or different halogen atoms and are, for example, trifluoromethyl, chlorodifluoromethyl, 2,2,2-trifluoro-ethyl or 2,2-difluoro-ethyl.

Haloalkenyl groups are alkenyl groups, respectively, which are substituted with one or more of the same or different halogen atoms and are, for example, 2,2-difluoro-vinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of (5-6 membered) monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably monocyclic rings containing 1 to 3 heterotoms selected from O, N or S, e.g. pyridyl, pyridazinyl, pyrimidinyl, pyrazinyl, pyrazolyl, furanyl, thiophenyl, oxazolyl, isoxazolyl, thiazolyl, preferably pyridyl, pyrazolyl, furanyl, thiophenyl, thiazolyl, pyridyl being most preferred.

The term "heterocyclyl" is defined to include heteroaryl and in addition their unsaturated or partially unsaturated analogues.

Preferred values of $A^1$, $A^2$, $A^3$, $A^4$, B, $R^1$, $R^2 R^3$, $R^4$ and $R^5$ are, in any combination, as set out below. These preferred values apply to all compounds of the invention having any or all of these substituents.

Preferably $A^1$ is C—H or C—$R^3$ and no more than two of $A^2$, $A^3$ and $A^4$ are nitrogen, more preferably no more than two of $A^2$, $A^3$ and $A^4$ are nitrogen and $A^3$ and $A^4$ are not both nitrogen. Even more preferably $A^1$ is C—H or C—$R^3$, $A^2$ is C—H, C—$R^3$ or nitrogen, $A^3$ and $A^4$ are independently C—H or nitrogen, wherein no more than two of $A^2$, $A^3$ and $A^4$ are nitrogen, and $A^3$ and $A^4$ are not both nitrogen, and wherein when $A^2$ is C—$R^3$ then the $R^3$ of $A^1$ and the $R^3$ of $A^2$ together form a —CH=CH—CH=CH— bridge. Yet even more preferably $A^1$ is C—$R^3$, $A^2$ is C—H, C—$R^3$ or nitrogen, $A^3$ and $A^4$ are independently C—H or nitrogen, wherein no more than two of $A^2$, $A^3$ and $A^4$ are nitrogen, and $A^3$ and $A^4$ are not both nitrogen, and wherein when $A^2$ is C—$R^3$ then the $R^3$ of $A^1$ and the $R^3$ of $A^2$ together form a —CH=CH—CH=CH— bridge. Yet even more preferably $A^1$ is C—$R^3$, $A^2$ is C—H, and one of $A^3$ and $A^4$ is C—H and the other is nitrogen.

In one group of compounds $A^1$ is C—H or C—$R^3$, most preferably $A^1$ is C—$R^3$.

In one group of compounds $A^2$ is C—H or C—$R^3$, most preferably $A^2$ is C—H.

In one group of compounds $A^3$ is C—H or C—$R^3$, most preferably $A^3$ is C—H.

In one group of compounds $A^4$ is C—H or C—$R^3$, most preferably $A^4$ is C—H.

Preferably $R^1$ is chlorodifluoromethyl, difluoromethyl or trifluoromethyl, more preferably chlorodifluoromethyl or trifluoromethyl, most preferably trifluoromethyl.

Preferably $R^2$ is aryl or aryl substituted by one to three $R^4$, more preferably $R^2$ is phenyl or phenyl substituted by one to three $R^4$, pyridyl or pyridyl substituted by one to three $R^4$, more preferably $R^2$ is phenyl substituted by one to three $R^4$ or pyridyl substituted by one to three $R^4$, more preferably $R^2$ is group P

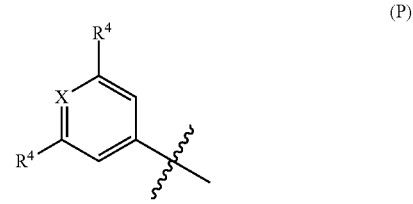

(P)

wherein X is N or C—$R^4$, preferably X is C—$R^4$.

More preferably $R^2$ is 3,5-bis-(trifluoromethyl)-phenyl, 3-chloro-5-trifluoromethyl-phenyl, 3-bromo-5-trifluoromethyl-phenyl, 3,5-dibromo-phenyl, 3,5-dichloro-phenyl, 3,4-dichloro-phenyl, 3-trifluoromethyl-phenyl, 4-bromo-3,5-dichlorophenyl, 3-bromo-5-chlorophenyl, 4-fluoro-3,5-dichlorophenyl or 3,4,5-trichloro-phenyl, 3-chloro-4-fluorophenyl, 3-fluoro-4-chlorophenyl, 4-bromo-3,5-dichlorophenyl, 4-iodo-3,5-dichlorophenyl, 3,4,5-trifluorophenyl, 3-chloro-5-fluorophenyl, 3,4-dichloro-5-trifluoromethylphenyl or 4-chloro-3,5-bis-(trifluoromethyl)-phenyl, more preferably 3,5-bis-(trifluoromethyl)-phenyl, 3-chloro-5-trifluoromethyl-phenyl, 3,5-dichloro-phenyl, 3-trifluoromethyl-phenyl, 4-bromo-3,5-dichlorophenyl, 3-bromo-5-chlorophenyl, 4-fluoro-3,5-dichlorophenyl, 3,4,5-trichloro-phenyl, 4-iodo-3,5-dichlorophenyl, 3,4-dichloro-5-trifluoromethylphenyl, 4-chloro-3,5-bis-(trifluoromethyl)-phenyl, most preferably $R^2$ is 3,5-dichlorophenyl.

Preferably each $R^3$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_1$-$C_8$alkoxy or $C_1$-$C_8$haloalkoxy, or two $R^7$ on adjacent carbon atoms together form a —CH=CH—

CH=CH— bridge, more preferably halogen, cyano, nitro, C₁-C₈alkyl, C₂-C₈ alkenyl, C₃-C₈cycloalkyl, C₁-C₈haloalkyl, C₁-C₈alkoxy or C₁-C₈haloalkoxy, even more preferably bromo, chloro, fluoro, cyano, nitro, methyl, ethyl, trifluoromethyl, cyclopropyl, vinyl, methoxy, trifluoromethoxy, yet even more preferably bromo, chloro, fluoro, cyclopropyl, trifluoromethyl, vinyl, or methyl, ethyl, nitro, cyano, most preferably bromo, chloro, fluoro, or methyl.

Preferably each R⁴ is independently halogen, cyano, nitro, C₁-C₈alkyl, C₁-C₈haloalkyl, C₁-C₈alkoxy, C₁-C₈haloalkoxy, more preferably iodo, bromo, chloro, fluoro, cyano, nitro, methyl, ethyl, trifluoromethyl, methoxy, difluoromethoxy, or trifluoromethoxy, most preferably bromo, chloro, fluoro, iodo or trifluoromethyl.

The compounds of formula IA and IB have a lower than expected log P value potentially leading to increased bioavailability.

Compounds of formula IA include at least one chiral centre and may exist as compounds of formula IA* or compounds of formula IA**. Compounds IA* and IA** are enantiomers if there is no other chiral center or epimers otherwise.

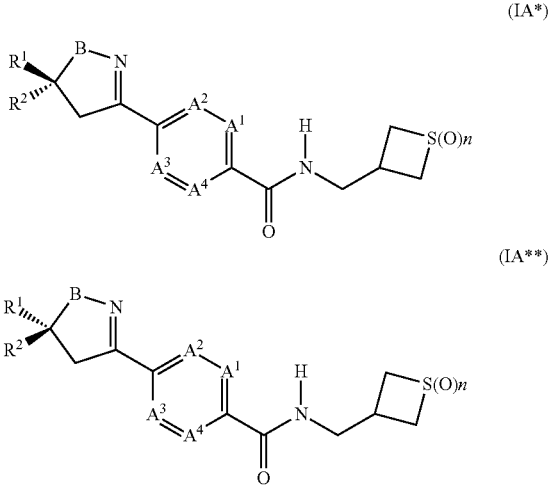

Compounds of formula IA** are more biologically active than compounds of formula IA*. The invention includes mixtures of compounds IA* and IA in any ratio e.g. in a molar ratio of 1:99 to 99:1, e.g. 10:1 to 1:10, e.g. a substantially 50:50 molar ratio. In an enantiomerically (or epimerically) enriched mixture of formula IA, the molar proportion of compound IA** compared to the total amount of both IA* and IA** is for example greater than 50%, e.g. at least 55, 60, 65, 70, 75, 80, 85, 90, 95, 96, 97, 98, or at least 99%. Likewise, in enantiomerically (or epimerically) enriched mixture of formula IA*, the molar proportion of the compound of formula IA* compared to the total amount of IA* and IA is for example greater than 50%, e.g. at least 55, 60, 65, 70, 75, 80, 85, 90, 95, 96, 97, 98, or at least 99%. Enantiomerically (or epimerically) enriched mixtures of formula IA are preferred.

Likewise, compounds of formula IB include at least one chiral centre and may exist as compounds of formula IB* or compounds of formula IB**. Compounds IB* and IB** are enantiomers if there is no other chiral center or epimers otherwise.

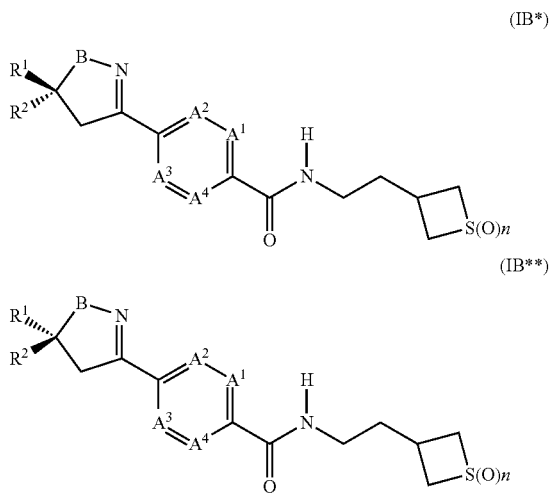

Compounds of formula IB** are more biologically active than compounds of formula IB*. The invention includes mixtures of compounds IB* and IB in any ratio e.g. in a molar ratio of 1:99 to 99:1, e.g. 10:1 to 1:10, e.g. a substantially 50:50 molar ratio. In an enantiomerically (or epimerically) enriched mixture of formula IB, the molar proportion of compound IB** compared to the total amount of both IB* and IB** is for example greater than 50%, e.g. at least 55, 60, 65, 70, 75, 80, 85, 90, 95, 96, 97, 98, or at least 99%. Likewise, in enantiomerically (or epimerically) enriched mixture of formula IB*, the molar proportion of the compound of formula IB* compared to the total amount of IB* and IB** is for example greater than 50%, e.g. at least 55, 60, 65, 70, 75, 80, 85, 90, 95, 96, 97, 98, or at least 99%.

Enantiomerically (or epimerically) enriched mixtures of formula IB** are preferred. The present invention includes all isomers of compounds of formula IA and IB, salts and N-oxides thereof, including enantiomers, diastereomers and tautomers. The compound of formula IA or IB may be a mixture of any type of isomer or may be substantially a single type of isomer. For example, where Y¹ or Y² is SO, the SO may be a mixture of the cis and trans isomer in any ratio, e.g. in a molar ratio of 1:99 to 99:1, e.g. 10:1 to 1:10, e.g. a substantially 50:50 molar ratio. For example, in trans enriched mixtures of the compound of formula IA or IB, e.g. when Y¹ or Y² is SO, the molar proportion of the trans compound in the mixture compared to the total amount of both cis and trans is for example greater than 50%, e.g. at least 55, 60, 65, 70, 75, 80, 85, 90, 95, 96, 97, 98, or at least 99%. Likewise, in cis enriched mixtures of the compound of formula IA or IB (cis enriched mixtures are preferred), e.g. when Y¹ or Y² is SO, the molar proportion of the cis compound in the mixture compared to the total amount of both cis and trans is for example greater than 50%, e.g. at least 55, 60, 65, 70, 75, 80, 85, 90, 95, 96, 97, 98, or at least 99%. The compound of formula IA or IB may be enriched for the trans sulphoxide. Likewise, the compound of formula IA or IB may be enriched for the cis sulphoxide.

Further details regarding the process steps are given below.

Scheme 1

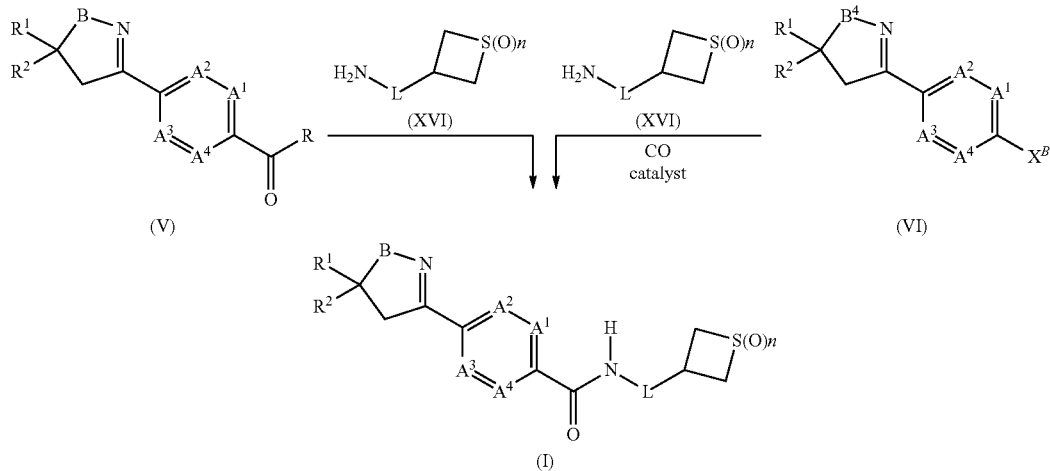

1) Compounds of formula (I) (i.e. compound of formula IA and IB) can be prepared by reacting a compound of formula (V) wherein R is OH, $C_1$-$C_6$alkoxy or Cl, F or Br, with an amine of formula (XVI), wherein L is methylene or ethylene, as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. It is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (XVI) are either known in the literature or can be prepared using methods known to a person skilled in the art. Some of these methods are described in the preparation examples.

2) Acid halides of formula (V), wherein R is Cl, F or Br, may be made from carboxylic acids of formula (V), wherein R is OH, under standard conditions, as described for example in WO2008/128711.

3) Carboxylic acids of formula (V), wherein R is OH, may be formed from esters of formula (V), wherein R is $C_1$-$C_6$alkoxy as described for example in WO2009/072621.

4) Compounds of formula (I) wherein, can be prepared by reacting a compound of formula (VI) wherein $X^B$ is a leaving group, for example a halogen, such as bromo, with carbon monoxide and an amine of formula (XVI), in the presence of a catalyst, such as palladium(II) acetate or bis-(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature from 50° C. to 200° C., preferably from 100° C. to 150° C. The reaction is carried out at a pressure from 50 to 200 bar, preferably from 100 to 150 bar.

5) Compounds of formula (VI) wherein $X^B$ is a leaving group, e.g. halogen, $C_1$-$C_8$alkoxy, $C_1$-$C_8$alkylsulfonyloxy, $C_1$-$C_8$haloalkylsulfonyloxy, $C_1$-$C_8$arylsulfonyloxy, optionally substituted $C_1$-$C_8$arylsulfonyloxy (aryl is preferably phenyl), diazonium salts (e.g. $X^B$ is —$N_2^+$ Cl$^-$, —$N_2^+$ BF$_4^-$, —$N_2^+$ Br$^-$, —$N_2^+$ PF$_6^-$), phosphonate esters (e.g. —OP(O)(OR$^x$)$_2$, wherein R$^x$ is methyl or ethyl), preferably bromo, iodo, chloro, trifluoromethylsulfoxy, p-toluenesulfoxy, diazonium chloride, preferably halogen, more preferably bromo, can be made by a various of methods, for example as described in WO2009/080250.

Scheme 2

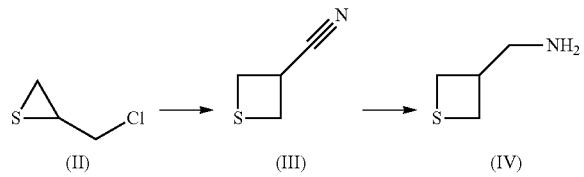

6) Thietan-3-nitrile (III) can be obtained by reaction of epithiochlorhydrin (II) with a cyanide M-CN, such as sodium cyanide or potassium cyanide in the presence of water, preferably as a co-solvent with an organic solvent such as benzene or tetrahydrofuran, at a temperature of 20° C. to 100° C., preferably 40-60° C. preferably around 50° C. Water is preferably used as a solvent, more preferably as a co-solvent with an organic solvent, preferably a water-immiscible organic solvent, e.g. such that the reaction then takes place in a biphasic system. The organic co-solvent is preferred to be aprotic, and is more preferably chosen from pentane, hexane, heptane, cyclohexane, benzene, toluene, xylene, tetrahydrofuran, ethyl acetate, diethyl ether, or methyl-tert-butyl ether. The reaction can be performed with an excess of epithiochlorhydrin or with an excess of M-CN, preferably in stoechiometric ratio or slight excess of one or the other reagent.

7) Compounds of formula (IV) can be prepared by reaction of compounds of formula (III) with a suitable reducing reagent. The most suitable, but not exclusive, method is the use of metal hydride reagents, such as lithium aluminum hydride or borane, in the presence or not of cocatalysts. Other methods that can be carried out involve the hydrogenation in the presence of Raney Ni, or palladium for instance. The most common solvents for this reaction are alcohols such as methanol or ethanol, tetrahydrofuran, toluene, ethers, such as diethyl ether or methyl tert-butyl ether. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

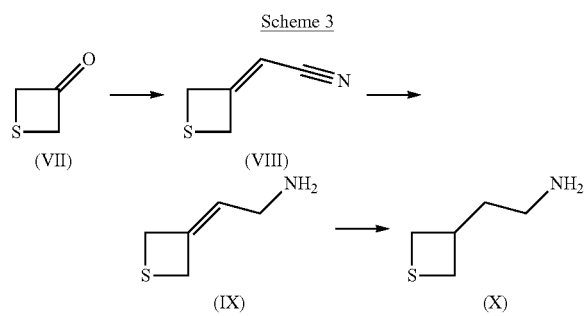

Scheme 3

8) Compounds of formula (VIII) can be obtained by various methods from the thietanone (VII). For example, they can be prepared by performing a wittig reaction or a related reaction, using (triphenylphosphoranylidene)acetonitrile or (Cyanomethyl)diethoxyphosphine oxide as a reagent or following a procedure in analogy to the one described in Organic Letters 2010, 12(9), 1944-1947 and Journal of the American Chemical Society 2009, 131(8), 2786-2787. Such reactions are usually performed in a solvent, such as toluene or dichloromethane, at a temperature of from 0° C. to 150° C., preferably from 0° C. to 50° C. Thietan-3-one (VII) can be prepared according to known methods, for example described in Synlett, (11), 783-4; 1991 or in WO 2007046548.

9) Compounds of formula (IX) can be prepared by reaction of compounds of formula (VIII) with a suitable reducing reagent. The most suitable, but not exclusive, method is the use of metal hydride reagents, such as sodium borohydride. Other methods that can be carried out involve the hydrogenation under a hydrogen atmosphere in the presence of palladium for instance. The most common solvents for this reaction are alcohols such as methanol or ethanol. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

10) Compounds of formula (X) can be prepared by reaction of compounds of formula (IX) with a suitable reducing reagent. The most suitable, but not exclusive, method is the use of metal hydride reagents, such as lithium aluminum hydride or borane, in the presence or not of cocatalysts. Other methods that can be carried out involve the hydrogenation in the presence of Raney Ni, or palladium for instance. The most common solvents for this reaction are alcohols such as methanol or ethanol, tetrahydrofuran, toluene, ethers, such as diethyl ether or methyl tert-butyl ether. In most cases it is advantageous to conduct the reaction at dilution between 0.1 M to 1 M, preferably 0.3 M to 0.5 M, at a temperature of 0° C. to 100° C., preferably 0-80° C. preferably around 20° C., and the reaction time in most cases is between 30 minutes and 12 hours.

11) Alternatively, compounds of formula (X) may be obtained directly by reduction of compounds of formula (VIII), for example under hydrogenation conditions, e.g. using hydrogen and a metal hydrogenation catalyst, e.g. Palladium, Rhodium, or Platinum.

Schemes 4 and 5 represent additional routes for the preparation of the amines.

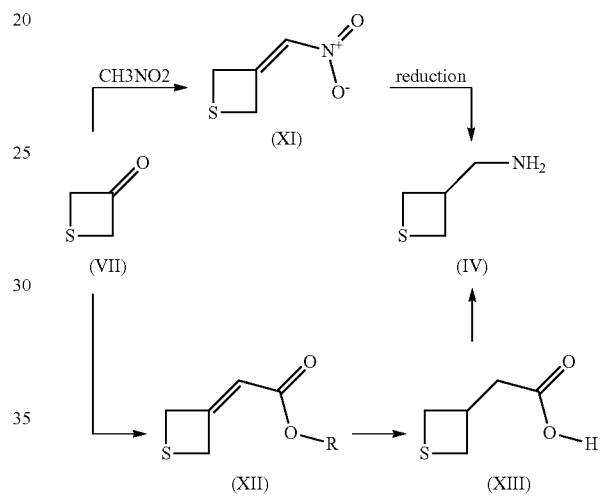

Scheme 4

12) Compound (IV) may be prepared by reduction of a nitromethylene compound of formula (XI). Reducing agents suitable for this reduction include for example metal hydride reagents such as sodium borohydride or lithium aluminium hydride optionally in the presence of a catalyst, for example nichel chloride. Hydrogenation in the presence of metal catalyst such as raney nickel or palladium on charcoal is an alternative for such reductions. Examples of such methods can be found in Journal of the American Chemical Society (2003), 125(40), 12125-12136, US patent no 20050261327, or in Journal of Medicinal Chemistry (2010), 53(7), 2942-2951.

13) Compounds of formula (XI) can be prepared by reaction of the ketone of formula (VII) with nitromethane under standard conditions (Henry reaction), as described for example in Angewandte Chemie, International Edition, 45(46), 7736-7739; 2006 or in Journal of Medicinal Chemistry, 53(8), 3227-3246; 2010.

14) Alternatively, the amine of formula (IV) may be obtained from the carboxylic acid of formula (XIII) using Schmidt or Curtius rearrangement. Schmidt rearrangement involves treatment with hydrazoic acid under a range of possible conditions known to the person skilled of the art, for example as described in Journal of Organic Chemistry, 58(6), 1372-6; 1993 for the conversion of bicyclo[1.1.1] pentane-2-carboxylic acid to bicyclo[1.1.1]pentane-2-amine. Curtius rearrangement can be carried out under different possible conditions known to the person skilled in the art, for example treatment of (XIII) with diphenylphosphoryl azide followed by heating and reaction with an alcohol such as benzyl alcohol or tert-butanol; the corresponding ester is obtained and subsequently deprotected to the amine by hydrogenolysis (benzyl ester) or treatment with trifluoroacetic acid (tert-butyl ester). Such conditions are for example described in Journal of Organic Chemistry, 75(17), 5941-5952, 2010 or Tetrahedron: Asymmetry, 14(23), 3773-3778; 2003.

15) The acid of formula (XIII) may derive from the ketone of formula (VII) after homologation of the ketone (VII) to an ester of formula (XII) (wherein R is $C_1$-$C_6$alkyl) followed by hydride reduction or hydrogenation of the double bond. Similar synthetic sequences from related substrates are described for example in Chemical & Pharmaceutical Bulletin, 52(6), 675-687; 2004, Synlett (2005), (10), 1559-1562, WO 2005019221, or WO 2010031735.

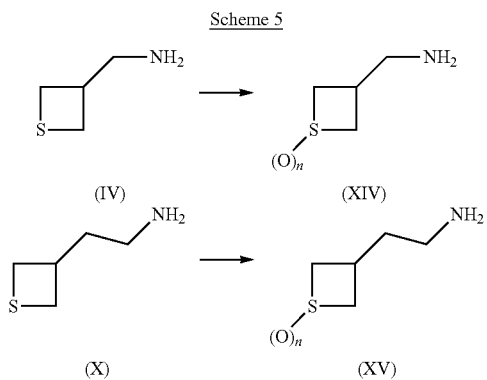

Scheme 5

16) Amines of formula (IV) and (X) may be converted to further amine intermediates of formula (XIV) and (XV) wherein n is 1 or 2. The amines may be directly oxidized or first protected, oxidized and then deprotected Compounds XIV and XV form further aspects of the invention.

The compounds according to the present invention show a potential inseciticidal action and can therefore be used as an insecticide. Furthermore, the compounds according to the present invention can exhibit a strong control effect against harmful insects, without substantially imposing any harmful side effects to cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof.

Harmful animal pest are for example:

As for insects, coleopterans, for example, *Callosobruchus chinensis, Sitophilus zeamais, Tribolium castaneum, Epilachna vigintioctomaculata, Agriotes fuscicollis, Anomala rufocuprea, Leptinotarsa decemlineata, Diabrotica* spp., *Monochamus alternatus, Lissorhoptrus oryzophilus, Lyctus bruneus, Aulacophora femoralis*; lepidopterans, for example, *Lymantria dispar, Malacosoma neustria), Pieris rapae, Spodoptera litura, Mamestra brassicae, Chilo suppressalis), Pyrausta nubilalis, Ephestia cautella, Adoxophyes orana, Carpocapsa pomonella, Agrotisfucosa, Galleria mellonella, Plutella maculipennis, Heliothis virescens, Phyllocnistis citrella*; hemipterans, for example, *Nephotettix cincticeps, Nilaparvata lugens, Pseudococcus comstocki, Unaspis yanonensis, Myzus persicas, Aphis pomi, Aphis gossypii, Rhopalosiphum pseudobrassicas, Stephanitis nashi, Nezara* spp., *Trialeurodes vaporariorm, Psylla* spp.; thysanopterans, for example, *Thrips palmi, Franklinella occidental*; orthopterans, for example, *Blatella germanica, Periplaneta americana, Gryllotalpa Africana, Locusta migratoria migratoriodes*; isopterans, for example, *Reticulitermes speratus, Coptotermes formosanus*; dipterans, for example, *Musca domestica, Aedes aegypti, Hylemia platura, Culex pipiens, Anopheles sinensis, Culex tritaeniorhynchus, Liriomyza trifolii*.

As for acari, for example, *Tetranychus cinnabarinus, Tetranychus urticae, Panonychus citri, Aculops pelekassi, Tarsonemus* spp.

As for nematodes, for example, *Meloidogyne incognita, Bursaphelenchus lignicolus Mamiya et Kiyohara, Aphelenchoides besseyi, Heterodera glycines, Pratylenchus* spp.

Additionally, the compounds according to the present invention may show a good plant tolerance and favourable toxicity to warm-blooded animals and being tolerated well by the environment, and thus are suitable for protecting plants and plant parts. Application of the compounds of the invention may result in increasing the harvest yields, improving the quality of the harvested material.

Additionally, the compounds can be used for controlling animal pests, in particular insects, arachnids, helminths, nematodes and molluscs, which are encountered in agriculture, in horticulture, the field of veterinary medicine, in forests, in gardens and leisure facilities, in the protection of stored products and of materials, and in the hygiene sector. They may preferably be employed as plant protection agents. They may be active against normally sensitive and resistant species and against all or some stages of development.

These pests include inter alia:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gaffinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscehdes obtectus, Adoretus* spp., *Agelastica* alni, *Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp.,

*Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It may be furthermore possible to control protozoa, such as *Eimeria*.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Caffigypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus haffi*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *lcerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Moneffia costalis*, *Moneffiopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Mono-morium pharaonis*, *Vespa* spp.

From the order of the Isopoda, for example, *Armadiffidium vulgare*, *Oniscus asellus*, *Porceffio scaber*.

From the order of the Isoptera, for example, *Reticulitermes* spp., *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Cheimatobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans*, *Xiphinema* spp.

All plants and plant parts can be treated in accordance with the invention.

Plants are to be understood as meaning in the present context all plants and plant populations such as desired and undesired wild plants or crop plants (including naturally occurring crop plants).

Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights.

Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes.

The plant parts also include harvested material, and vegetative and generative propagation material, for example cuttings, tubers, rhizomes, offshoots and seeds. Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

In a preferred embodiment, wild plant species and plant cultivars, or those obtained by conventional biological breeding methods, such as crossing or protoplast fusion, and parts thereof, are treated.

In a further preferred embodiment, transgenic plants and plant cultivars obtained by genetic engineering methods, if appropriate in combination with conventional methods (Genetically Modified Organisms), and parts thereof, are treated. Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques.

These can be cultivars, bio- or genotypes. Depending on the plant species or plant cultivars, their location and growth conditions (soils, climate, vegetation period, diet), the treatment according to the invention may also result in super-additive "synergistic" effects.

Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products.

Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds.

Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape.

Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants").

Traits that are also particularly emphasized are the increased defence of the plants against fungi, bacteria and viruses by systemic acquired resistance (SAR), systemin, phytoalexins, elicitors and resistance genes and correspondingly expressed proteins and toxins.

Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants.

Examples of "Bt plants" which may be mentioned are maize varieties, cotton varieties, soya bean varieties and potato varieties which are sold under the trade names YIELD GARD(®) (for example maize, cotton, soya beans), KnockOut(®) (for example maize), StarLink(®) (for example maize), Bollgard(®) (cotton), Nucotn(®) (cotton) and NewLeaf(®) (potato).

Examples of herbicide-tolerant plants which may be mentioned are maize varieties, cotton varieties and soya bean varieties which are sold under the trade names Roundup Ready(®) (tolerance to glyphosate, for example maize, cotton, soya beans), Liberty Link(®) (tolerance to phosphinotricin, for example oilseed rape), IMI(®) (tolerance to imidazolinones) and STS(®) (tolerance to sulphonylureas, for example maize).

Herbicide-resistant plants (plants bred in a conventional manner for herbicide tolerance) which may be mentioned include the varieties sold under the name Clearfield(®) (for example maize).

These statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

Furthermore, in the field of veterinary medicine, the novel compounds of the present invention can be effectively used against various harmful animal parasitic pests (endoparasites and ectoparasites), for example, insects and helminthes.

Examples of such animal parasitic pests include the pests as described below.

Examples of the insects include *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*, and the like.

Examples of acari include *Ornithodoros* spp., *Ixodes* spp., *Boophilus* spp., and the like.

In the veterinary fields, e.g. in the field of veterinary medicine, the active compounds according to the present invention are active against animal parasites, in particular ectoparasites or endoparasites.

The term endoparasites includes in particular helminths, such as cestodes, nematodes or trematodes, and protozoae, such as coccidia.

Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus*, *Linognathus vituli*, *Linognathus ovillus*, *Linognathus oviformis*, *Linognathus pedalis*, *Linognathus stenopsis*, *Haematopinus asini macrocephalus*, *Haematopinus eurysternus*, *Haematopinus suis*, *Pediculus humanus capitis*, *Pediculus humanus corporis*, *Phylloera vastatrix*, *Phthirus pubis*, *Solenopotes capillatus*; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis*, *Bovicola ovis*, *Bovicola limbata*, *Damalina bovis*, *Trichodectes canis*, *Felicola subrostratus*, *Bovicola caprae*, *Lepikentron ovis*, *Werneckiella equi*; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti*, *Aedes albopictus*, *Aedes taeniorhynchus*, *Anopheles gambiae*, *Anopheles maculipennis*, *Calliphora erythrocephala*, *Chrysozona pluvialis*, *Culex quinquefasciatus*, *Culex pipiens*, *Culex tarsalis*, *Fannia canicularis*, *Sarcophaga carnaria*, *Stomoxys calcitrans*, *Tipula paludosa*, *Lucilia cuprina*, *Lucilia sericata*, *Simulium reptans*, *Phlebotomus papatasi*, *Phlebotomus longipalpis*, *Odagmia ornata*, *Wilhelmia equina*, *Boophthora erythrocephala*, *Tabanus bromius*, *Tabanus spodopterus*, *Tabanus atratus*, *Tabanus sudeticus*, *Hybomitra ciurea*, *Chrysops caecutiens*, *Chrysops relictus*, *Haematopota pluvialis*, *Haematopota italica*, *Musca autumnalis*, *Musca domestica*, *Haematobia irritans irritans*, *Haematobia irritans exigua*, *Haematobia stimulans*, *Hydrotaea irritans*, *Hydrotaea albipuncta*, *Chrysomya chloropyga*, *Chrysomya bezziana*, *Oestrus ovis*, *Hypoderma bovis*, *Hypoderma lineatum*, *Przhevalskiana silenus*, *Dermatobia hominis*, *Melophagus ovinus*, *Lipoptena capreoli*, *Lipoptena cervi*, *Hippobosca variegata*, *Hippobosca equina*, *Gasterophilus intestinalis*, *Gasterophilus haemorroidalis*, *Gasterophilus inermis*, *Gasterophilus nasalis*, *Gasterophilus nigricornis*, *Gasterophilus pecorum*, *Braula coeca*; from the order of the Siphonapterida, for example *Pulex* spp., *Ctenocephalides* spp., *Tunga* spp., *Xenopsylla* spp., *Ceratophyllus* spp.; particular examples are: *Ctenocephalides canis*, *Ctenocephalides felis*, *Pulex irritans*, *Tunga penetrans*, *Xenopsylla cheopis*; from the order of the Heteropterida, for example *Cimex* spp., *Triatoma* spp., *Rhodnius* spp., *Panstrongylus* spp.

From the order of the Blattarida, for example *Blatta orientalis*, *Periplaneta americana*, *Blattela germanica*, *Supella* spp. (e.g. *Suppella longilpalpa*);

From the subclass of the *Acari* (*Acarina*) and the orders of the Meta- and Mesostigmata, for example *Argas* spp., *Ornithodorus* spp., *Otobius* spp., *Ixodes* spp., *Amblyomma* spp., *Rhipicephalus* (*Boophilus*) spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus*, *Argas reflexus*, *Ornithodorus moubata*, *Otobius megnini*, *Rhipicephalus* (*Boophilus*) *microplus*, *Rhipicephalus* (*Boophilus*) *decoloratus*, *Rhipicephalus* (*Boophilus*) *annulatus*, *Rhipicephalus* (*Boophilus*) *calceratus*, *Hyalomma anatolicum*, *Hyalomma aegypticum*, *Hyalomma marginatum*, *Hyalomma transiens*, *Rhipicephalus evertsi*, *Ixodes ricinus*, *Ixodes hexagonus*, *Ixodes canisuga*, *Ixodes pilosus*, *Ixodes rubicundus*, *Ixodes scapularis*, *Ixodes holocyclus*, *Haemaphysalis concinna*, *Haemaphysalis punctata*, *Haemaphysalis cinnabarina*, *Haemaphysalis otophila*, *Haemaphysalis leachi*, *Haemaphysalis longicomi*, *Dermacentor marginatus*, *Dermacentor reticulatus*, *Dermacentor pictus*, *Dermacentor albipictus*, *Dermacentor andersoni*, *Dermacentor variabilis*, *Hyalomma mauritanicum*, *Rhipicephalus sanguineus*, *Rhipicephalus bursa*, *Rhipicephalus appendiculatus*, *Rhipicephalus capensis*, *Rhipicephalus turanicus*, *Rhipicephalus zambeziensis*, *Amblyomma americanum*, *Amblyomma variegatum*, *Amblyomma maculatum*, *Amblyomma hebraeum*, *Amblyomma cajennense*, *Dermanyssus gaffinae*, *Ornithonyssus bursa*, *Ornithonyssus sylviarum*, *Varroa jacobsoni*; from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are:

*Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals.

Animals include agricultural livestock such as, for example, cattle, sheep, goats, horses, pigs, donkeys, camels, buffaloes, rabbits, chickens, turkeys, ducks, geese, cultured fish, honeybees.

Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it may be desirable to prevent or interrupt the uptake of blood by the parasites from the hosts.

Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels.

More specifically, "controlling", as used herein, means that the active compound is effective in killing the respective parasite, inhibiting its growth, or inhibiting its proliferation. Generally, when used for the treatment of animals the active compounds according to the invention can be applied directly.

Preferably they are applied as pharmaceutical compositions which may contain pharmaceutically acceptable excipients and/or auxiliaries which are known in the art.

In the veterinary field and in animal keeping, the active compounds are applied (e.g. administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like.

The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80 percent by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

In the present invention, a substance having an insecticidal action against pests including all of these is referred to as an insecticide.

An active compound of the present invention can be prepared in conventional formulation forms, when used as an insecticide.

Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), ULV (cold mist, warm mist), and the like. These formulations can be produced by methods that are known per se.

For example, a formulation can be produced by mixing the active compound with a developer, that is, a liquid diluent or carrier; a liquefied gas diluent or carrier; a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like. The liquefied gas diluent or carrier may be those which are gaseous at normal temperature and normal pressure, for example, aerosol propellants such as butane, propane, nitrogen gas, carbon dioxide and halogenated hydrocarbons. Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like. Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like. Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydro lyzate, and the like. Examples of the dispersant include lignin sulfite waste liquor and methylcellulose.

Fixing agents can also be used in the formulations (powders, granules, emulsions), and examples of the fixing agent include carboxymethylcellulose, natural and synthetic polymers (for example, gum arabic, polyvinyl alcohol, polyvinyl acetate, and the like) and the like. Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc. The formulations in general can contain the active ingredient in an amount ranging from 0.1 to 95 percent by weight, and preferably 0.5 to 90 percent> by weight. The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100 percent by weight, and preferably 0.00001 to 1 percent by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil. The compounds of the invention may have favourable properties with respect to amount appled, residue formulation, selectivity, toxicity, production methodology, high activity, wide spectrum of control, safety, control of resistant organisms, e.g. pests that are resistant to organic phosphorus agents and/or carbamate agents.

Further embodiments of the invention are described below.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leaf miner), *Musca domestica* (housefly), *Aedes aegypti* (mosquito), *Anopheles* spp. (mosquitoes), *Culex* spp. (mosquitoes), *Luciffia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus*, and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The compounds of the invention may be used for pest control on various plants, including soybean (e.g. in some cases 10-70 g/ha), corn (e.g. in some cases 10-70 g/ha), sugarcane (e.g. in some cases 20-200 g/ha), alfalfa (e.g. in some cases 10-70 g/ha), brassicas (e.g. in some cases 10-50 g/ha), oilseed rape (e.g. canola) (e.g. in some cases 20-70 g/ha), potatoes (including sweet potatoes) (e.g. in some cases 10-70 g/ha), cotton (e.g. in some cases 10-70 g/ha), rice (e.g. in some cases 10-70 g/ha), coffee (e.g. in some cases 30-150 g/ha), citrus (e.g. in some cases 60-200 g/ha), almonds (e.g. in some cases 40-180 g/ha), fruiting vegetables (e.g. tomatoes, pepper, chili, eggplant, cucumber, squash etc.) (e.g. in some cases 10-80 g/ha), tea (e.g. in some cases 20-150 g/ha), bulb vegetables (e.g. onion, leek etc.) (e.g. in some cases 30-90 g/ha), grapes (e.g. in some cases 30-180 g/ha), pome fruit (e.g. apples, pears etc.) (e.g. in some cases 30-180 g/ha), and stone fruit (e.g. pears, plums etc.) (e.g. in some cases 30-180 g/ha).

The compounds of the invention may be used on soybean to control, for example, *Elasmopalpus lignosellus, Diloboderus abderus, Diabrotica speciosa, Sternechus subsignatus, Formicidae, Agrotis ypsilon, Julus* ssp., *Anticarsia gemmatalis, Megascelis* ssp., *Procornitermes* ssp., *Gryllotalpidae, Nezara viridula, Piezodorus* spp., *Acrosternum* spp., *Neomegalotomus* spp., *Cerotoma trifurcate, Popillia japonica, Edessa* spp., *Liogenys fuscus, Euchistus heros*, stalk borer, *Scaptocoris castanea, phyllophaga* spp., *Pseudoplusia includens, Spodoptera* spp., *Bemisia tabaci, Agriotes* spp. The compounds of the invention are preferably used on soybean to control *Diloboderus abderus, Diabrotica speciosa, Nezara viridula, Piezodorus* spp., *Acrosternum* spp., *Cerotoma trifurcata, Popillia japonica, Euchistus heros, phyllophaga* spp., *Agriotes* spp.

The compounds of the invention may be used on corn to control, for example, *Euchistus heros, Dichelops furcatus, Diloboderus abderus, Elasmopalpus lignosellus, Spodoptera frugiperda, Nezara viridula, Cerotoma trifurcata, Popiffia japonica, Agrotis ypsilon, Diabrotica speciosa, Heteroptera, Procornitermes* ssp., *Scaptocoris castanea, Formicidae, Julus* ssp., *Dalbulus maidis, Diabrotica virgifera, Mocis latipes, Bemisia tabaci, heliothis* spp., *Tetranychus* spp., *thrips* spp., *phyllophaga* spp., *scaptocoris* spp., *Liogenys fuscus, Spodoptera* spp., *Ostrinia* spp., *Sesamia* spp., *Agriotes* spp. The compounds of the invention are preferably used on corn to control *Euchistus hems, Dichelops furcatus, Diloboderus abderus, Nezara viridula, Cerotoma trifurcata, Popiffia japonica, Diabrotica speciosa, Diabrotica virgifera, Tetranychus* spp., *thrips* spp., *phyllophaga* spp., *scaptocoris* spp., *Agriotes* spp.

The compounds of the invention may be used on sugar cane to control, for example, *Sphenophorus* spp., termites, *Mahanarva* spp. The compounds of the invention are preferably used on sugar cane to control termites, *Mahanarva* spp.

The compounds of the invention may be used on alfalfa to control, for example, *Hypera brunneipennis, Hypera postica, Colias eurytheme, Collops* spp., *Empoasca solana, Epitrix, Geocoris* spp., *Lygus hesperus, Lygus lineolaris, Spissistilus* spp, *Spodoptera* spp., *Trichoplusia ni*. The compounds of the invention are preferably used on alfalfa to control *Hypera brunneipennis, Hypera postica, Empoasca solana, Epitrix, Lygus hesperus, Lygus lineolaris, Trichoplusia ni*.

The compounds of the invention may be used on brassicas to control, for example, *Plutella xylostella, Pieris* spp., *Mamestra* spp., *Plusia* spp., *Trichoplusia ni, Phyllotreta* spp., *Spodoptera* spp., *Empoasca solana, thrips* spp., *Spodoptera* spp., *Delia* spp. The compounds of the invention are preferably used on brassicas to control *Plutella xylostella Pieris* spp., *Plusia* spp., *Trichoplusia ni, Phyllotreta* spp., *thrips* spp.

The compounds of the invention may be used on oil seed rape, e.g. canola, to control, for example, *Meligethes* sp, *Ceutorhynchus napi, Psylloides* sp.

The compounds of the invention may be used on potatoes, including sweet potatoes, to control, for example, *Empoasca* sp, *Leptinotarsa* sp, *Diabrotica speciosa, Phthorimaea* sp, *Paratrioza* sp, *Maladera matrida, Agriotes* sp. The compounds of the invention are preferably used on potatoes, including sweet potatoes, to control *Empoasca* sp, *Leptinotarsa* sp, *Diabrotica speciosa, Phthorimaea* sp, *Paratrioza* sp, *Agriotes* sp.

The compounds of the invention may be used on cotton to control, for example, *Anthonomus grandis, Pectinophora* sp, *heliothis* sp, *Spodoptera* sp, *Tetranychus* sp, *Empoasca* sp, *thrips* sp, *Bemisia tabaci, Lygus* sp, *phyllophaga* sp, *Scaptocoris* sp. The compounds of the invention are preferably used on cotton to control *Anthonomus grandis, Tetranychus* sp, *Empoasca* sp, *thrips* sp, *Lygus* sp, *phyllophaga* sp, *Scaptocoris* sp.

The compounds of the invention may be used on rice to control, for example, *Leptocorisa* sp, *Cnaphalocrosis* sp, *Chilo* sp, *Scirpophaga* sp, *Lissorhoptrus* sp, *Oebalus pugnax*. The compounds of the invention are preferably used on rice to control *Leptocorisa* sp, *Lissorhoptrus* sp, *Oebalus pugnax*.

The compounds of the invention may be used on coffee to control, for example, *Hypothenemus Hampei, Perileucoptera Coffeella, Tetranychus* sp. The compounds of the invention are preferably used on coffee to control *Hypothenemus Hampei, Perileucoptera Coffeella*.

The compounds of the invention may be used on citrus to control, for example, *Panonychus citri, Phyllocoptruta oleivora, Brevipalpus* sp, *Diaphorina citri, Scirtothrips* sp, *thrips* sp, *Unaspis* sp, *Ceratitis capitata, Phyllocnistis* sp. The compounds of the invention are preferably used on citrus to control *Panonychus citri, Phyllocoptruta oleivora, Brevipalpus* sp, *Diaphorina citri, Scirtothrips* sp, *thrips* sp, *Phyllocnistis* sp.

The compounds of the invention may be used on almonds to control, for example, *Amyelois transitella, Tetranychus* sp.

The compounds of the invention may be used on fruiting vegetable, including tomatoes, pepper, chili, eggplant, cucumber, squash etc, to control *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Bemisia tabaci, Trialeurodes* sp, *Paratrioza* sp, *Frankliniella occidentalis, Frankliniella* sp, *Anthonomus* sp, *Phyllotreta* sp, *Amrasca* sp, *Epilachna* sp, *Halyomorpha* sp, *Scirtothrips* sp, *Leucinodes* sp, *Neoleucinodes* sp. The compounds of the invention are preferably used on fruiting vegetable, including tomatoes, pepper, chili, eggplant, cucumber, squash etc, to control, for example, *thrips* sp, *Tetranychus* sp, *Polyphagotarsonemus* sp, *Aculops* sp, *Empoasca* sp, *Spodoptera* sp, *heliothis* sp, *Tuta absoluta, Liriomyza* sp, *Paratrioza* sp, *Frankliniella occidentalis, Frankliniella* sp, *Amrasca* sp, *Scirtothrips* sp, *Leucinodes* sp, *Neoleucinodes* sp.

The compounds of the invention may be used on tea to control, for example, *Pseudaulacaspis* sp, *Empoasca* sp, *Scirtothrips* sp, *Caloptilia theivora*. The compounds of the invention are preferably used on tea to control *Empoasca* sp, *Scirtothrips* sp.

The compounds of the invention may be used on bulb vegetables, including onion, leek etc to control, for example, *thrips* sp, *Spodoptera* sp, *heliothis* sp. The compounds of the invention are preferably used on bulb vegetables, including onion, leek etc to control *thrips* sp.

The compounds of the invention may be used on grapes to control, for example, *Empoasca* sp, *Lobesia* sp, *Frankliniella* sp, *thrips* sp, *Tetranychus* sp, *Rhipiphorothrips Cruentatus, Eotetranychus Willamettei, Erythroneura Elegantula, Scaphoides* sp. The compounds of the invention are preferably used on grapes to control *Frankliniella* sp, *thrips* sp, *Tetranychus* sp, *Rhipiphorothrips Cruentatus, Scaphoides* sp.

The compounds of the invention may be used on pome fruit, including apples, pairs etc, to control, for example, *Cacopsylla* sp, *Psylla* sp, *Panonychus ulmi, Cydia pomonella*. The compounds of the invention are preferably used on pome fruit, including apples, pairs etc, to control *Cacopsylla* sp, *Psylla* sp, *Panonychus ulmi*.

The compounds of the invention may be used on stone fruit to control, for example, *Grapholita molesta, Scirtothrips* sp, *thrips* sp, *Frankliniella* sp, *Tetranychus* sp. The compounds of the invention are preferably used on stone fruit to control *Scirtothrips* sp, *thrips* sp, *Frankliniella* sp, *Tetranychus* sp.

The compounds of the invention may be used to control animal housing pests including: Ants, Bedbugs (adult), Bees, Beetles, Boxelder Bugs, Carpenter Bees, Carpet Beetles, Centipedes, Cigarette, Beetles, Clover Mites, Cockroaches, Confused Flour Beetle, Crickets, Earwigs, Firebrats, Fleas, Flies, Lesser Grain Borers, Millipedes, Mosquitoes, Red Flour Beetles, Rice Weevils, Saw-toothed Grain Beetles, Silverfish, Sowbugs, Spiders, Termites, Ticks, Wasps, Cockroaches, Crickets, Flies, Litter Beetles (such as Darkling, Hide, and Carrion), Mosquitoes, Pillbugs, Scorpions, Spiders, Spider Mites (Twospotted, Spruce), Ticks.

The compounds of the invention may be used to control ornamental pests including: Ants (Including Imported fire ants), Armyworms, Azalea caterpillars, Aphids, Bagworms, Black vine weevils (adult), Boxelder bugs, Budworms, California oakworms, Cankerworms, Cockroaches, Crickets, Cutworms, Eastern tent caterpillars, Elm leaf beetles, European sawflies, Fall webworms, Flea beetles, Forest tent caterpillars, Gypsy moth larvae, Japanese beetles (adults), June beetles (adults), Lace bugs, Leaf-feeding caterpillars, Leafhoppers, Leaf miners (adults), Leaf rollers, Leaf skeletonizers, Midges, Mosquitoes, Oleander moth larvae, Pillbugs, Pine sawflies, Pine shoot beetles, Pinetip moths, Plant bugs, Root weevils, Sawflies, Scale insects (crawlers), Spiders, Spittlebugs, Striped beetles, Striped oakworms, Thrips, Tip moths, Tussock moth larvae, Wasps, Broadmites, Brown softscales, California redscales (crawlers), Clover mites, Mealybugs, Pineneedlescales (crawlers), Spider mites, Whiteflies The compounds of the invention may be used to control turf pests including: Ants (Including Imported fire ants, Armyworms, Centipedes, Crickets, Cutworms, Earwigs, Fleas (adult), Grasshoppers, Japanese beetles (adult), Millipedes, Mites, Mosquitoes (adult), Pillbugs, Sod webworms, Sow bugs, Ticks (including species which transmit Lyme disease), Bluegrass billbugs (adult), Black turfgrass ataenius (adult), Chiggers, Fleas (adult), Grubs (suppression), Hyperodes weevils (adult), Mole crickets (nymphs and young adults), Mole Crickets (mature adults), Chinch Bugs.

The invention therefore provides a method of combating and/or controlling an animal pest, e.g. an invertebrate animal pest, which comprises applying to the pest, to a locus of the pest, or to a plant susceptible to attack by the pest a pesticidally effective amount of a compound of formula (I). In particular, the invention provides a method of combating and/or controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees. Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is generally used at a rate of 0.0001 g to 10 g (for example 0.001 g or 0.05 g), preferably 0.005 g to 10 g, more preferably 0.005 g to 4 g, per kilogram of seed.

In another aspect the present invention provides a composition comprising a pesticidally effective amount of a compound of formula (I), in particular an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, e.g. a insecticide, fungicide or herbicide, or a synergist or plant growth regulator where appropriate. An additional active ingredient may provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following (where "Tx" means a compound of formula (I), which may result in a synergistic combination with the given active ingredient):

a) Pyrethroids, wherein suitable combinations include permethrin+Tx, cypermethrin+Tx, fenvalerate+Tx, esfenvalerate+Tx, deltamethrin+Tx, cyhalothrin+Tx (in particular lambda-cyhalothrin+Tx and gamma cyhalothrin+Tx), bifenthrin+Tx, fenpropathrin+Tx, cyfluthrin+Tx, tefluthrin+Tx, fish safe pyrethroids+Tx (for example ethofenprox+Tx), natural pyrethrin+Tx, tetramethrin+Tx, S-bioallethrin+Tx, fenfluthrin+Tx, prallethrin+Tx or 5-benzyl-3-furylmethyl-(E)-(1R,3S)-2,2-dimethyl-3-(2-oxothiolan-3-ylidenemethyl)cyclopropane carboxylate+Tx;

b) Organophosphates, wherein suitable combinations include profenofos+Tx, sulprofos+Tx, acephate+Tx, methyl parathion+Tx, azinphos-methyl+Tx, demeton-s-methyl+Tx, heptenophos+Tx, thiometon+Tx, fenamiphos+Tx, monocrotophos+Tx, profenofos+Tx, triazophos+Tx, methamidophos+Tx, dimethoate+Tx, phosphamidon+Tx, malathion+Tx, chlorpyrifos+Tx, phosalone+Tx, terbufos+Tx, fensulfothion+Tx, fonofos+Tx, phorate+Tx, phoxim+Tx, pirimiphos-methyl+Tx, pirimiphos-ethyl+Tx, fenitrothion+Tx, fosthiazate+Tx or diazinon+Tx;

c) Carbamates (including aryl carbamates), wherein suitable combinations include pirimicarb+Tx, triazamate+Tx, cloethocarb+Tx, carbofuran+Tx, furathiocarb+Tx, ethiofencarb+Tx, aldicarb+Tx, thiofurox+Tx, carbosulfan+Tx, bendiocarb+Tx, fenobucarb+Tx, propoxur+Tx, methomyl+Tx or oxamyl+Tx;

d) Benzoyl ureas, wherein suitable combinations include diflubenzuron+Tx, triflumuron+Tx, hexaflumuron+Tx, flufenoxuron+Tx, lufeneron+Tx or chlorfluazuron+Tx;

e) Organic tin compounds, wherein suitable combinations include cyhexatin+Tx, fenbutatin oxide+Tx or azocyclotin+Tx;

f) Pyrazoles, wherein suitable combinations include tebufenpyrad+Tx and fenpyroximate+Tx;

g) Macrolides, such as avermectins or milbemycins, wherein suitable combinations include for example abamectin+Tx, emamectin benzoate+Tx, ivermectin+Tx, milbemycin+Tx, spinosad+Tx, azadirachtin+Tx or spinetoram+Tx;

h) Hormones or pheromones;

i) Organochlorine compounds, wherein suitable combinations include endosulfan+Tx (in particular alpha-endosulfan+Tx), benzene hexachloride+Tx, DDT+Tx, chlordane+Tx or dieldrin+Tx;

j) Amidines, wherein suitable combinations include chlordimeform+Tx or amitraz+Tx;

k) Fumigant agents, wherein suitable combinations include chloropicrin+Tx, dichloropropane+Tx, methyl bromide+Tx or metam+Tx;

l) Neonicotinoid compounds, wherein suitable combinations include imidacloprid+Tx, thiacloprid+Tx, acetamiprid+Tx, nitenpyram+Tx, dinotefuran+Tx, thiamethoxam+Tx, clothianidin+Tx or nithiazine+Tx;

m) Diacylhydrazines, wherein suitable combinations include tebufenozide+Tx, chromafenozide+Tx or methoxyfenozide+Tx;

n) Diphenyl ethers, wherein suitable combinations include diofenolan+Tx or pyriproxifen+Tx;

o) Indoxacarb+Tx;

p) Chlorfenapyr+Tx;

q) Pymetrozine+Tx or flonicamid+Tx;

r) Spirotetramat+Tx, spirodiclofen+Tx or spiromesifen+Tx;

s) Diamides, wherein suitable combinations include flubendiamide+Tx, chlorantraniliprole(Rynaxypyr®)+Tx or cyantraniliprole+Tx;

t) Sulfoxaflor+Tx; or u) Metaflumizone+Tx;

v) Fipronil+Tx and Ethiprole+Tx;

w) Pyrifluqinazon+Tx;

x) buprofezin+Tx; or y) 4-[(6-Chloro-pyridin-3-ylmethyl)-(2,2-difluoro-ethyl)-amino]-5H-furan-2-one (DE 102006015467)+Tx.

In addition to the major chemical classes of pesticide listed above, other pesticides having particular targets may be employed in the composition, if appropriate for the intended utility of the composition. For instance, selective insecticides for particular crops, for example stemborer specific insecticide (combinations such as cartap+Tx) or hopper specific insecticides (combinations such as buprofezin+Tx) for use in rice may be employed. Alternatively insecticides or acaricides specific for particular insect species/stages may also be included in the compositions (for example acaricidal ovo-larvicides, to give combinations such as clofentezine+Tx, flubenzimine+Tx, hexythiazox+Tx or tetradifon+Tx; acaricidal motilicides, to give combinations such as dicofol+Tx or propargite+Tx; acaricides, to give combinations such as bromopropylate+Tx or chlorobenzilate+Tx; or growth regulators, such as hydramethylnon+Tx, cyromazine+Tx, methoprene+Tx, chlorfluazuron+Tx or diflubenzuron+Tx).

Examples of fungicidal compounds and combinations which may be included in the composition of the invention are (E)-N-methyl-2-[2-(2,5-dimethylphenoxymethyl)phenyl]-2-methoxy-iminoacetamide (SSF-129)+Tx, 4-bromo-2-cyano-N,N-dimethyl-6-trifluoromethylbenzimidazole-1-sulfonamide+Tx, α-[N-(3-chloro-2,6-xylyl)-2-methoxyacetamido]-γ-butyrolactone+Tx, 4-chloro-2-cyano-N,N-dimethyl-5-p-tolylimidazole-1-sulfonamide (IKF-916, cyamidazosulfamid)+Tx, 3-5-dichloro-N-(3-chloro-1-ethyl-1-methyl-2-oxopropyl)-4-methylbenzamide (RH-7281, zoxamide)+Tx, N-allyl-4,5,-dimethyl-2-trimethylsilylthiophene-3-carboxamide (MON65500)+Tx, N-(1-cyano-1,2-dimethylpropyl)-2-(2,4-dichlorophenoxy)propionamide (AC382042)+Tx, N-(2-methoxy-5-pyridyl)-cyclopropane carboxamide+Tx, acibenzolar (CGA245704) (e.g. acibenzolar-S-methyl)+Tx, alanycarb+Tx, aldimorph+Tx, anilazine+Tx, azaconazole+Tx, azoxystrobin+Tx, benalaxyl+Tx, benomyl+Tx, benthiavalicarb+Tx, biloxazol+Tx, biterta-nol+Tx, bixafen+Tx, blasticidin S+Tx, boscalid+Tx, bromuconazole+Tx, bupirimate+Tx, captafol+Tx, captan+Tx, carbendazim+Tx, carbendazim+Tx, chlorhydrate+Tx, carboxin+Tx, carpropamid+Tx, carvone+Tx, CGA41396+Tx, CGA41397+Tx, chinomethionate+Tx, chlorothalonil+Tx, chlorozolinate+Tx, clozylacon+Tx, copper containing compounds to give combintations such as copper oxychloride+Tx, copper oxyquinolate+Tx, copper sulfate+Tx, copper tallate+Tx and Bordeaux mixture+Tx, cyclufenamid+Tx, cymoxanil+Tx, cyproconazole+Tx, cyprodinil+Tx, debacarb+Tx, di-2-pyridyl disulfide 1,1'-dioxide+Tx, dichlofluanid+Tx, diclomezine+Tx, dicloran+Tx, diethofencarb+Tx, difenoconazole+Tx, difenzoquat+Tx, diflumetorim+Tx, O,O-di-iso-propyl-S-benzyl thiophosphate+Tx, dimefluazole+Tx, dimetconazole+Tx, dimethomorph+Tx, dimethirimol+Tx, diniconazole+Tx, dinocap+Tx, dithianon+Tx, dodecyl dimethyl ammonium chloride+Tx, dodemorph+Tx, dodine+Tx, doguadine+Tx, edifenphos+Tx, epoxiconazole+Tx, ethirimo+Tx I, ethyl-(Z)—N-benzyl-N-([methyl(methyl-thioethylideneamino-oxycarbonyl)amino]thio)-β-alaninate+Tx, etridiazole+Tx, famoxadone+Tx, fenamidone (RPA407213)+Tx, fenarimol+Tx, fenbuconazole+Tx, fenfuram+Tx, fenhexamid (KBR2738)+Tx, fenpiclonil+Tx, fenpropidin+Tx, fenpropimorph+Tx, fentin acetate+Tx, fentin hydroxide+Tx, ferbam+Tx, ferimzone+Tx, fluazinam+Tx, fludioxonil+Tx, flumetover+Tx, fluopyram+Tx, fluoxastrobin+Tx, fluoroimide+Tx, fluquinconazole+Tx, flusilazole+Tx, flutolanil+Tx, flutriafol+Tx, fluxapyroxad+Tx, folpet+Tx, fuberidazole+Tx, furalaxyl+Tx, furametpyr+Tx, guazatine, +Tx hexaconazole+Tx, hydroxyisoxazole+Tx, hymexazole+Tx, imazalil+Tx, imibenconazole+Tx, iminoctadine+Tx, iminoctadine triacetate+Tx, ipconazole+Tx, iprobenfos+Tx, iprodione+Tx, iprovalicarb (SZX0722)+Tx, isopropanyl butyl carbamate+Tx, isoprothiolane+Tx, isopyrazam+Tx, kasugamycin+Tx, kresoxim-methyl+Tx, LY186054+Tx, LY211795+Tx, LY248908+Tx, mancozeb+Tx, mandipropamid+Tx, maneb+Tx, mefenoxam+Tx, metalaxyl+Tx, mepanipyrim+Tx, mepronil+Tx, metalaxyl+Tx, metconazole+Tx, metiram+Tx, metiram-zinc+Tx, metominostrobin+Tx, myclobutanil+Tx, neoasozin+Tx, nickel dimethyldithiocarbamate+Tx, nitrothal-isopropyl+Tx, nuarimol+Tx, ofurace+Tx, organomercury compounds, +Tx oxadixyl+Tx, oxasulfuron+Tx, oxolinic acid+Tx, oxpoconazole+Tx, oxycarboxin+Tx, pefurazoate+Tx, penconazole+Tx, pencycuron+Tx, penflufen+Tx, penthiopyrad+Tx, phenazin oxide+Tx, phosetyl-Al+Tx, phosphorus acids+Tx, phthalide+Tx, picoxystrobin (ZA1963)+Tx, polyoxinD+Tx, polyram+Tx, probenazole+Tx, prochloraz+Tx, procymidone+Tx, propamocarb+Tx, propiconazole+Tx, propineb+Tx, propionic acid+Tx, prothioconazole+Tx, pyrazophos+Tx, pyrifenox+Tx, pyrimethanil+Tx, pyraclostrobin+Tx, pyroquilon+Tx, pyroxyfur+Tx, pyrrolnitrin+Tx, quaternary ammonium compounds+Tx, quinomethionate+Tx, quinoxyfen+Tx, quintozene+Tx, sedaxane+Tx, sipconazole (F-155)+Tx, sodium pentachlorophenate+Tx, spiroxamine+Tx, streptomycin+Tx, sulfur+Tx, tebuconazole+Tx, tecloftalam+Tx, tecnazene+Tx, tetraconazole+Tx, thiabendazole+Tx, thifluzamid+Tx, 2-(thiocyanomethylthio)benzothiazole+Tx, thiophanate-methyl+Tx, thiram+Tx, timibenconazole+Tx, tolclofos-methyl+Tx, tolylfluanid+Tx, triadimefon+Tx, triadimenol+Tx, triazbutil+Tx, triazoxide+Tx, tricyclazole+Tx, tridemorph+Tx, trifloxystrobin (CGA279202)+Tx, triforine+Tx, triflumizole+Tx, triticonazole+Tx, validamycin A+Tx, vapam+Tx, vinclozolin+Tx, zineb+Tx and ziram+Tx, N-[9-(dichloromethylene)-1,2,3,4-tetrahydro-1,4-methanonaphthalen-5-yl]-3-(difluoromethyl)-1-methyl-1H-pyrazole-4-carboxamide [1072957-71-1]+Tx, 1-methyl-3-difluoromethyl-1H-pyrazole-4-carboxylic acid (2-dichloromethylene-3-ethyl-1-methyl-indan-4-yl)-amide+Tx, and 1-methyl-3-difluoromethyl-4H-pyrazole-4-carboxylic acid [2-(2,4-dichloro-phenyl)-2-methoxy-1-methyl-ethyl]-amide+Tx.

The active ingredients combinations described above comprising a compound selected of the invention and an active ingredient as described above are preferably combined in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The compounds of the invention are also useful in the field of animal health, e.g. they may be used against parasitic invertebrate pests, more preferably against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention provides a compound of the invention for use in a method of therapeutic treatment.

In a further aspect the invention relates to a method of controlling parasitic invertebrate pests in or on an animal comprising administering a pesticidally effective amount of a compound of the invention. The administration may be for example oral administration, parenteral administration or external administration, e.g. to the surface of the animal body. In a further aspect the invention relates to a compound of the invention for controlling parasitic invertebrate pests in or on an animal. In a further aspect the invention relates to use of a compound of the invention in the manufacture of a medicament for controlling parasitic invertebrate pests in or on an animal In a further aspect, the invention relates to a method of controlling parasitic invertebrate pests comprising administering a pesticidally effective amount of a compound of the invention to the environment in which an animal resides.

In a further aspect the invention relates to a method of protecting an animal from a parasitic invertebrate pest comprising administering to the animal a pesticidally effective amount of a compound of the invention. In a further aspect the invention relates to a compound of the invention for use in protecting an animal from a parasitic invertebrate pest. In a further aspect the invention relates to use of a compound of the invention in the manufacture of a medicament for protecting an animal from a parasitic invertebrate pest.

In a further aspect the invention provides a method of treating an animal suffering from a parasitic invertebrate pest comprising administering to the animal a pesticidally effective amount of a compound of the invention. In a further aspect the invention relates to a compound of the invention for use in treating an animal suffering from a parasitic invertebrate pest. In a further aspect the invention relates to use of a compound of the invention in the manufacture of a medicament for treating an animal suffering from a parasitic invertebrate pest.

In a further aspect, the invention provides a pharmaceutical composition comprising a compound of the invention and a pharmaceutically suitable excipient.

The compounds of the invention may be used alone or in combination with one or more other biologically active ingredients.

In one aspect the invention provides a combination product comprising a pesticidally effective amount of a component A and a pesticidally effective amount of component B wherein component A is compound of formula I and component B is a compound as described below.

The compounds of the invention may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in International Patent Application Publication Numbers WO95/19363 or WO04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: *Bacillus thuringiensis* ssp aizawai, kurstaki, *Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

When used in combination with other active ingredients, the compounds of the invention are preferably used in combination with the following (where "Tx" means a compound of formula (I) which may result in a synergistic combination with the given active ingredient): imidacloprid+Tx, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, fipronil+Tx, ivermectin+Tx, omeprazole+Tx, tiamulin+Tx, benazepril+Tx, milbemycin+Tx, cyromazine+Tx, thiamethoxam+Tx, pyriprole+Tx, deltamethrin+Tx, cefquinome+Tx, florfenicol+Tx, buserelin+Tx, cefovecin+Tx, tulathromycin+Tx, ceftiour+Tx, selamectin+Tx, carprofen+Tx, metaflumizone+Tx, moxidectin+Tx, methoprene (including S-methoprene)+Tx, clorsulon+Tx, pyrantel+Tx, amitraz+Tx, triclabendazole+Tx, avermectin+Tx, abamectin+Tx, emamectin+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, fipronil+Tx, lufenuron+Tx, ecdysone+Tx or tebufenozide+Tx; more preferably, enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx, pyrantel+Tx, eprinomectin+Tx, doramectin+Tx, selamectin+Tx, nemadectin+Tx, albendazole+Tx, cambendazole+Tx, fenbendazole+Tx, flubendazole+Tx, mebendazole+Tx, oxfendazole+Tx, oxibendazole+Tx, parbendazole+Tx, tetramisole+Tx, levamisole+Tx, pyrantel pamoate+Tx, oxantel+Tx, morantel+Tx, triclabendazole+Tx, epsiprantel+Tx, lufenuron+Tx or ecdysone+Tx; even more preferably enrofloxacin+Tx, praziquantel+Tx, pyrantel embonate+Tx, febantel+Tx, penethamate+Tx, moloxicam+Tx, cefalexin+Tx, kanamycin+Tx, pimobendan+Tx, clenbuterol+Tx, omeprazole+Tx, tiamulin+Tx, benazepril+Tx, pyriprole+Tx, cefquinome+Tx, florfenicol+Tx, buserelin+Tx, cefovecin+Tx, tulathromycin+Tx, ceftiour+Tx, selamectin+Tx, carprofen+Tx, moxidectin+Tx, clorsulon+Tx or pyrantel+Tx.

Examples of ratios include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

Of particular note is a combination where the additional active ingredient has a different site of action from the compound of formula I. In certain instances, a combination with at least one other parasitic invertebrate pest control active ingredient having a similar spectrum of control but a different site of action will be particularly advantageous for resistance management. Thus, a combination product of the invention may comprise a pesticidally effective amount of a compound of formula I and pesticidally effective amount of at least one additional parasitic invertebrate pest control active ingredient having a similar spectrum of control but a different site of action.

One skilled in the art recognizes that because in the environment and under physiological conditions salts of chemical compounds are in equilibrium with their corresponding non salt forms, salts share the biological utility of the non salt forms. Thus a wide variety of salts of compounds of the invention (and active ingredients used in combination with the active ingredients of the invention) may be useful for control of invertebrate pests and animal parasites. Salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The compounds of the invention also include N-oxides. Accordingly, the invention comprises combinations of compounds of the invention including N-oxides and salts thereof and an additional active ingredient including N-oxides and salts thereof.

The compositions for use in animal health may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

The compounds of the invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Compositions with spray oils, spray oil concentrations, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a pesticidally effective amount of a compound of the invention and a carrier. One embodiment of such a spray composition comprises a pesticidally effective amount of a compound of the invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The compounds of the invention may be particularly suitable for combating external parasitic pests. The compounds of the invention may be suitable for systemic and/or non-systemic control of infestation or infection by parasites on animals.

The compounds of the invention may be suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the compounds of the invention allows more economic and simple husbandry of animals.

The compounds of the invention may be suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the compounds of the invention can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" is understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the compounds of the invention to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals. Nematodes that are contemplated to be treated by the compounds of the invention include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma.*

Cestodes that are contemplated to be treated by the invention and by the inventive methods include, without limitation, the following genera: *Diphyllobothrium, Diplydium, Spirometra* and *Taenia.*

The most common genera of parasites of the gastrointestinal tract of humans are *Ancylostoma, Necator, Ascaris, Strongy hides, Trichinella, Capillaria, Trichuris* and *Enterobius.* Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella.*

Numerous other helminth genera and species are known to the art, and are also contemplated to be treated by the compounds of the invention. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The compounds of the invention may be effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans,* the horse fly or *Tabanus* spp., the stable fly or *Stomoxys calcitrans,* the black fly or *Simulium* spp., the deer fly or *Chrysops* spp., the louse fly or *Melophagus ovinus,* and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax,* the cattle grub or *Hypoderma* spp., the fleeceworm and the Gastrophilus of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi.*

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabillis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides fells*); *Xenopsylla* spp. such as oriental rat flea (*Xenopsylla cheopis*); and *Pulex* spp. such as human flea (*Pulex irritans*).

True bugs include, e.g., Cimicidae or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

Numerous other parasitic invertebrate pests are known to the art, and are also contemplated to be treated by the compounds of the invention. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The compounds of the invention may also be effective against ectoparasites including: flies such as *Haematobia (Lyperosia) irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (*Damalinia*) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

When compounds of the invention are applied in combination with an additional biologically active ingredient, they may be administered separately e.g. as separate compositions. In this case, the biologically active ingredients may be administered simultaneously or sequentially. Alternatively, the biologically active ingredients may be components of one composition.

The compounds of the invention may be administered in a controlled release form, for example in subcutaneous or orally administered slow release formulations.

Typically a parasiticidal composition according to the present invention comprises a compound of the invention, optionally in combination with an additional biologically active ingredient, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note are compounds of the invention for protecting an animal from an invertebrate parasitic pest comprising a parasitically effective amount of a compound of the invention, optionally in combination with an additional biologically active ingredient and at least one carrier.

For parenteral administration including intravenous, intramuscular and subcutaneous injection, the compounds of the invention can be formulated in suspension, solution or emulsion in oily or aqueous vehicles, and may contain adjuncts such as suspending, stabilizing and/or dispersing agents.

The compounds of the invention may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the invention may also be formulated as a depot preparation. Such long acting formulations may be administered by implantation (for example, subcutaneously or intramuscularly) or by intramuscular or subcutaneous injection.

The compounds of the invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount.

Capsules and cartridges of, for example, gelatin for use in an inhaler or insufflator may be formulated containing a powder mix of the compound and a suitable powder base such as lactose or starch.

The compounds of the invention may have favourable pharmacokinetic and pharmacodynamic properties providing systemic availability from oral administration and ingestion. Therefore after ingestion by the animal to be protected, parasiticidally effective concentrations of a compound of the invention in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the compounds of the invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

In one embodiment a composition of the present invention is formulated into a chewable and/or edible product (e.g., a chewable treat or edible tablet). Such a product would ideally have a taste, texture and/or aroma favored by the animal to be protected so as to facilitate oral administration of the compounds of the invention.

If the parasiticidal compositions are in the form of feed concentrates, the carrier is typically selected from high-performance feed, feed cereals or protein concentrates.

Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compound of the invention may also be formulated in rectal compositions such as suppositories or retention enemas, using, e.g., conventional suppository bases such as cocoa butter or other glycerides.

The formulations for the method of this invention may include an antioxidant, such as BHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (e.g. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the compounds of the invention are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the compositions of the present invention administered at suitable intervals typically ranges from about 0.01 mg/kg to about 100 mg/kg, and preferably from about 0.01 mg/kg to about 30 mg/kg of animal body weight.

Suitable intervals for the administration of the compositions of the present invention to animals range from about daily to about yearly. Of note are administration intervals ranging from about weekly to about once every 6 months. Of particular note are monthly adminstration intervals (i.e. administering the compounds to the animal once every month)s.

It has now been found, surprisingly, that the animal health active ingredient mixtures according to the invention not only delivers about the additive enhancement of the spectrum of action with respect to the pest to be controlled that was in principle to be expected but achieves a synergistic effect which can extend the range of action of the component A and of the component B in two ways. Firstly, the rates of application of the component A and of the component B are lowered whilst the action remains equally good. Secondly, the active ingredient mixture still achieves a high degree of pest control, sometimes even where the two individual components have become totally ineffective in such a low application rate range. This allows increased safety in use.

This synergistic effect applies in particular to mixtures where component A is a compound of formula I and component B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide. More preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone. Even more preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

The following Examples illustrate, but do not limit, the invention.

EXPERIMENTAL PROCEDURES

Example A.1: Thietane-3-carbonitrile

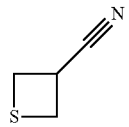

To a solution of epithiochlorohydrine (2.7 g) in benzene (10 ml) was added at room temperature a solution of potassium cyanide (4 g) in water (10 ml). The resulting mixture was heated to 50° C. for 12 hours. The mixture was extracted with benzene then the organic phase was washed with aqueous saturated sodium hydrogenocarbonate solution then water and brine. The organic phase was dried with sodium sulphate then the solvent was evaporated to dryness to give the crude residue as a yellow oil (1.76 g). 1 g of the crude was purified by a flash chromatography to obtain the title product as a brown solid (0.5 g). $^1$H-NMR (CDCl$_3$, 400 MHz): 3.25-3.35 (m, 2H), 3.65-3.75 (m, 2H), 4.10-4.25 (m, 1H). $^1$H-NMR (CDCl$_3$, 100 MHz) 27.3 (1C), 28.7 (2C), 119.7 (1C). GCMS (Method C): rt=5.07 min (87%) m/z: [M-CN]$^+$=73; [M+1]$^+$=100.

Example A.2: Thietane-3-carbonitrile

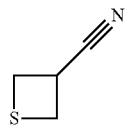

To a solution of epithiochlorohydrine (5.4 g) in tetrahydrofuran (20 ml) was added at room temperature a solution of potassium cyanide (4.9 g) in water (20 ml). The resulting mixture was heated to 50° C. for 12 hr. The mixture was extracted with tetrahydrofuran then the organic phase was washed with aqueous saturated sodium hydrogenocarbonate solution then water and brine. The organic phase was dried with sodium sulphate then the solvent was evaporated to dryness to give the crude title product as a violet oil (3.75 g), which was analysed by NMR and GCMS (see example A.1) and contained ca 10% of 2-aminothiophene.

Example B: Thietan-3-ylmethanamine

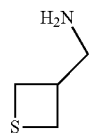

To a solution of lithium aluminium hydride (540 mg) in diethyl ether (30 ml) was added in a suspension of thietane-3-carbonitrile (1.4 g) in diethyl ether (30 ml) at 0° C. then the mixture was stirred at room temperature for 30 min. The mixture was then diluted with ether (50 ml), cooled to 0° C. then water (0.55 ml), 15% aqueous sodium hydroxide (0.55 ml) and water (1.60 ml) were added. The mixture was allowed to warm to room temperature and stirred for 15 min. Anhydrous magnesium sulphate was added and stirring was continued for 15 min, then the suspension was filtered on a celite pad. The solvent was evaporated to dryness to give the crude title product as an oil (980 mg). $^1$H-NMR (CDCl$_3$, 400 MHz): 3.21 (m, 3H); 3.00 (m, 2H); 2.86 (m, 2H).

Example C: 2-(thietan-3-ylidene)acetonitrile

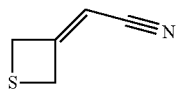

To a solution of thietan-3-one (900 mg) in 10 ml of dry methylene chloride was added a solution of (triphenylphosphoranylidene)acetonitrile (3.31 g) in 20 ml of dry methylene chloride at 0° C. The solution was allowed to warm to room temperature and after stirring for 15 min the solvent was removed under reduced pressure. The residue was purified by a flash chromatography (silica gel: Dichloromethane as an eluant) to give the title compound (785 mg) as a yellow-brown oil. GC/MS (Method C): rt=2.89 min (54.7%) m/z: [M+1]$^+$=112. $^1$H-NMR (CDCl$_3$, 400 MHz): 5.11 (m, 1H), 4.15 (m, 2H), 4.03 (m, 2H).

Example D: 2-(thietan-3-yl)acetonitrile

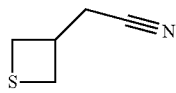

To a stirred solution of 2-(thietan-3-ylidene)acetonitrile (2.775 g) in dry methanol (250 mL), cooled to 0° C., was added sodium borohydride (9.250 g) in small portions over 30 min. The reaction mixture was allowed to warm to room temperature and stirred for a further hour.

The solvent was removed under reduced pressure. The purple residue was dissolved in ethyl acetate (50 ml) and extracted with saturated sodium hydrogenocarbonate (2×50 ml). The organic layer, dried over sodium sulphate, filtered and the solvent was removed under reduced pressure to yield a oil yellow. The residue was purified by a flash chromatography (silica gel: cyclohexane/ethyl acetate as an eluant) to give the title compound (2.2 g) as a yellow oil. GC/MS (Method C): rt=5.99 min (100%) m/z: [M+1]$^+$=114. $^1$H-NMR (CDCl$_3$, 400 MHz): 3.56 (m, 1H), 3.35 (dd, 2H), 3.09 (dd, 2H), 2.55 (d, 2H).

Example E: 2-(thietan-3-yl)ethanamine

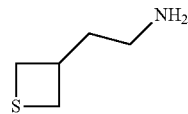

To a solution of lithium aluminium hydride (76 mg) in diethyl ether (4 ml) was added in a suspension of 2-(thietan-3-yl)acetonitrile (226 mg) in diethyl ether (30 ml) at 0° C. then the mixture was stirred at room temperature until the end of the gas evolution. The mixture was then diluted with ether (6 ml), cooled to 0° C. then water (0.08 ml), 15% aqueous sodium hydroxide (0.08 ml) and water (0.25 ml) were added. The mixture was allowed to warm to room temperature and stirred for 15 min. Anhydrous magnesium sulphate was added and stirring was continued for 15 min, then the suspension was filtered on a celite pad. The solvent was evaporated to dryness to give the crude title product as a brown oil (196 mg). $^1$H-NMR (CDCl$_3$, 400 MHz): 3.4-3.35 (m, 1H); 3.20-3.10 (2H); 3.1-3.0 (m, 2H); 2.6 (m, 2H). GC/MS (Method C): rt=5.80 min (90%) m/z: [M+1]$^+$=118.

Example F: Method for Preparing Compounds of the Invention from a Carboxylic Acid 4-[5-(3,5-dichlorophenyl)-5-(trifluoromethyl)-4H-isoxazol-3-yl]-2-methyl-N-(thietan-3-ylmethyl)benzamide

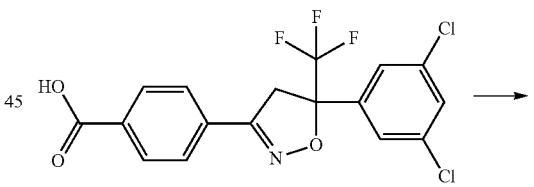

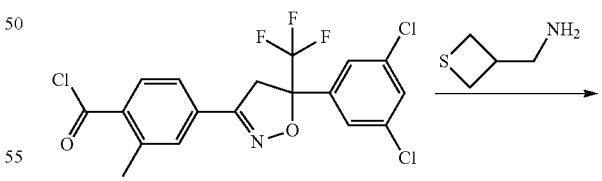

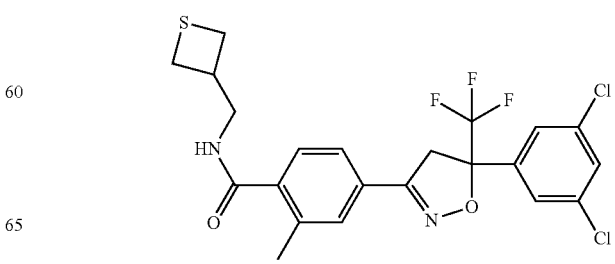

To a suspension of 4-[5-(3,5-dichloro-phenyl)-5-trifluoromethyl-4,5-dihydro-isoxazol-3-yl]-benzoic acid (836 mg, prepared as described for example in WO200/9080250) in dichloromethane (30 ml) was added oxalyl chloride (280 mg) and then one drop of N,N-dimethylformamide. The reaction mixture stirred at room temperature until the solids were dissolved, and the solvent was evaporated in vacuo to give a solid, which was dissolved in dichloromethane (10 ml) and the resulting solution added dropwise to a solution of triethylamine (0.5 ml) and thietan-3ylmethanamine (example B, 250 mg) in dichloromethane (20 ml) at room temperature, under argon. The reaction was stirred overnight at room temperature, diluted with water, and the organic layer washed with 1N hydrochloric acid solution, then with 1N sodium hydroxide solution, then with brine. The organic phase dried over anhydrous sodium sulfate, filtered and concentrated in vacuo. Purification by column chromatography (eluent heptane/ethyl acetate) afforded the title compound as a solid (570 mg). $^1$H-NMR (CDCl$_3$, 400 MHz): 7.60-7.40 (m, 6H), 6.02 (m, 1H), 4.10 (d, 1H), 3.70 (d, 1H), 3.65 (t, 2H), 3.55 (m, 1H), 3.33 (t, 2H), 3.05 (dd, 2H), 2.50 (s, 3H).

Example G: 4-[5-(3,5-dichlorophenyl)-5-(trifluoromethyl)-4H-isoxazol-3-yl]-2-methyl-N-(1.1-dioxothietan-3-ylmethyl)benzamide

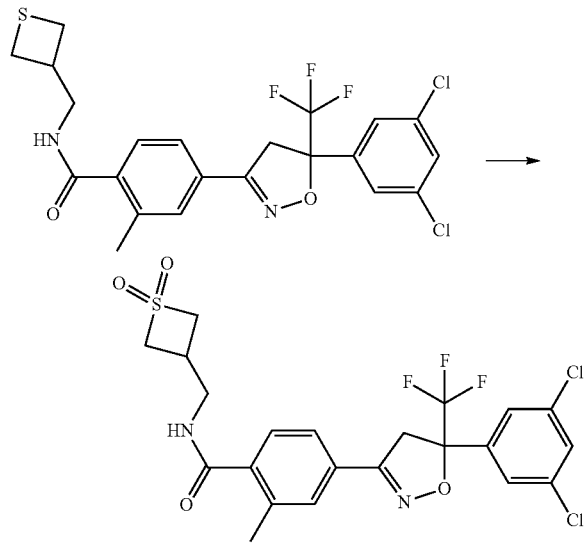

To a solution of 4-[5-(3,5-dichlorophenyl)-5-(trifluoromethyl)-4H-isoxazol-3-yl]-2-methyl-N-(thietan-3-ylmethyl)benzamide (505 mg) in dichloromethane (50 ml) at 0° C. was added a solution of sodium hydrogenocarbonate (504 mg) in water (10 ml) then 3-chloroperbenzoic acid (70% w/w, 615 mg). The resulting mixture was allowed to stir at room temperature for 1 hour. The reaction mixture was then extracted with dichloromethane then the organic phase was washed twice with water, dried over anhydrous sodium sulfate, filtered and evaporated to give the crude product as a solid. Purification by chromatography using the ISCO Rf machine (dichloromethane then 5% methanol) afforded the title product (300 mg) as a white solid. $^1$H-NMR (CDCl$_3$, 400 MHz): 7.60-7.40 (m, 6H), 6.25 (m, 1H), 4.30 (dd, 2H), 4.10 (d, 1H), 4.00 (dd, 2H), 3.75 (t, 2H), 3.72 (d, 1H), 3.00 (m, 1H), 2.50 (s, 3H).

Example H: 4-[(5S)-5-(3,5-dichlorophenyl)-5-(trifluoromethyl)-4H-isoxazol-3-yl]-2-methyl-N-(1,1-dioxothietan-3-ylmethyl)benzamide (compound H1)

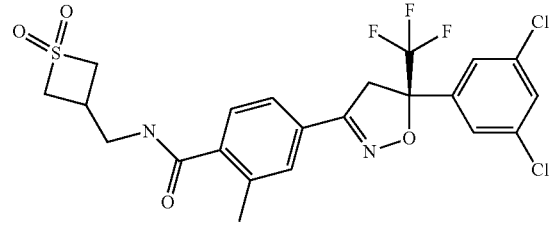 [SMILES: Cc1cc(C2=NO[C@](c3cc(Cl)cc(Cl)c3)(C(F)(F)F)C2)ccc1C(=O)NCC1CS(=O)(=O)C1]

Step A: 4-[(5S)-5-(3,5-dichlorophenyl)-5-(trifluoromethyl)-4H-isoxazol-3-yl]-2-methyl-N-(thietan-3-ylmethyl)benzamide

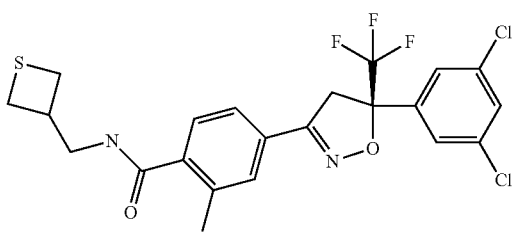 [SMILES: Cc1cc(C2=NO[C@](c3cc(Cl)cc(Cl)c3)(C(F)(F)F)C2)ccc1C(=O)NCC1CSC1]

To a suspension of 4-[(5S)-5-(3,5-dichlorophenyl)-5-(trifluoromethyl)-4H-isoxazol-3-yl]-2-methyl-N-(thietan-3-ylmethyl)benzoic acid (prepared as described in WO 2011067272, 8.36 g, ee 90%) in dichloromethane (225 ml) and a drop of DMF under argon atmosphere at room temperature, was added dropwise oxalylchloride (3.05 g) then the resulting mixture was stirred until the solid was dissolved (2 hours). The solution was concentrated in vacuo and the residue was dissolved in dichloromethane (100 ml), and added dropwise over 1 hour to a solution of thietan-3-ylmethanamine (prepared as described in Step B, 3.98 g) and triethylamine (8.62 ml) in dry dichloromethane (275 ml) at room temperature. The reaction mixture was quenched with an addition of 200 ml of water then the organic phase was washed 3 times with 50 ml saturated aqueous sodium hydrogenocarbonate solution, water and brine solution then dried over sodium sulphate. The solvent was removed under reduced pressure to dryness to give 10 g of a crude residue, which was purified by column chromatography (ethyl acetate, heptane) to afford the title product (8 g) as a white solid. $^1$H-NMR (CDCl$_3$, 400 MHz): 2.48 (s, 3H), 3.07 (m, 2H), 3.32 (m, 2H), 3.55 (m, 1H), 3.64 (t, 2H), 3.71 (d, 1H), 4.11 (d, 1H), 6.10 (br t, 1H), 7.40-7.60 (m, 6H).

Step B: 4-[(5S)-5-(3,5-dichlorophenyl)-5-(trifluoromethyl)-4H-isoxazol-3-yl]-2-methyl-N-(1,1-dioxothietan-3-ylmethyl)benzamide

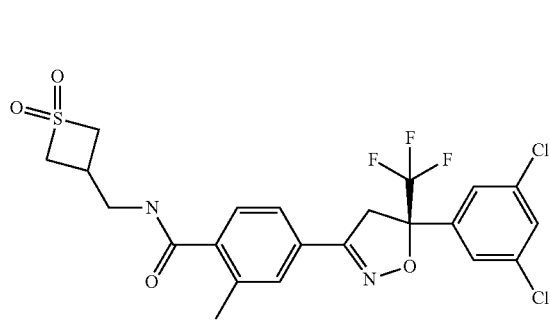 [SMILES: Cc1cc(C2=NO[C@](c3cc(Cl)cc(Cl)c3)(C(F)(F)F)C2)ccc1C(=O)NCC1CS(=O)(=O)C1]

To a solution of 4-[(5S)-5-(3,5-dichlorophenyl)-5-(trifluoromethyl)-4H-isoxazol-3-yl]-2-methyl-N-(thietan-3-ylmethyl)benzamide (13 g) in dichloromethane (500 ml) at 0° C. was added a solution of meta-chloroperbenzoic acid in dichloromethane (200 ml). The resulting mixture was allowed to room temperature and stirred for one night. The reaction mixture was washed twice with water, dried over anhydrous sodium sulfate, filtered and evaporated to give a crude residue, which was purified by column chromatography (ethyl acetate, heptane) to afford the title product (13.5 g) as a white solid. $^1$H-NMR (CDCl$_3$, 400 MHz): 2.38 (s, 3H), 2.90 (m, 1H), 3.60-3.70 (m, 3H), 3.85-3.92 (m, 2H), 4.00 (d, 1H), 4.19 (m, 2H), 6.20 (br t, 1H), 7.30-7.50 (m, 6H). Chiral HPLC analysis using a Waters UPLC—Hclass, DAD Detector Waters UPLC. Column: Daicel CHIRAL-PAK® IA, 3 ⌊ m, 0.46 cm×10 cm. Mobile phase: TBME/EtOH 98/02. Flow rate: 1.0 ml/min. Detection: 266. Sample concentration: 1 mg/mL in Hept/iPrOH 50/50. Injection: 2 ⌊ L. Peak 1: 9.15 min; 92.4%; Peak 2: 10.39 min; 7.6%.

Example I: (1,1-dioxothietan-3-yl)methanamine

Step A: Synthesis of 1,1-dioxothietan-3-carbonitrile

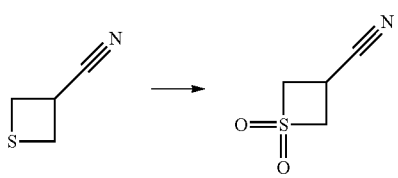 [SMILES: N#CC1CSC1 ; N#CC1CS(=O)(=O)C1]

3-cyano-thietane (198 mg) in dichloromethane (50 ml) at 0° C. was treated portionwise with meta-chloroperbenzoic acid (0.9 g) and the resulting solution was stirred overnight at room temperature. The mixture was poured into diluted aqueous sodium hydrogencarnonate solution, extracted with dichloromethane. Combined organic layers were dried over sodium sulphate, then the solvent was evaporated to afford the crude title product as a white solid.

1H NMR (CDCl$_3$): 4.45 (m, 4H); 3.40 (m, 1H).

Step B: Synthesis of (1,1-dioxothietan-3-yl)methanamine

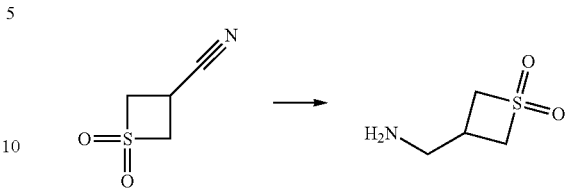

1,1-dioxothietane-3-carbonitrile (0.1 g) dissolved in methanol (45 ml) was passed through H-Cube equipped with a Ra—Ni cartridge at 50 bars, 1 ml/min and room temperature. The reaction mixture was poured into HCl (4M in dioxane) and after evaporation of the solvent, 60 mg of (1,1-dioxothietan-3-yl)methanamine hydrochloride as a yellow solid was obtained. 1H NMR (D$_2$O): 4.49-4.49 (m, 2H); 4.2-4.07 (m, 2H); 3.46 (d, 1H, J=7.3 Hz); 3.34 (d, 1H, J=7.3 Hz); 3.12-2.93 (m, 1H).

GC/MS Methods:
Method C

| Volatile CI/EI | GCMS was conducted on a Thermo, MS: DSQ and GC: TRACE GC ULTRA with a column from Zebron phenomenex: Phase ZB-5 ms 15 m, diam: 0.25 mm, 0.25 μm, H$_2$ flow 1.7 ml/min, temp injector: 250° C., temp detector: 220° C., method: hold 2 min at 40° C., 25° C./min until 320° C., hold 1 min 12 s at 320° C., total time 15 min. CI reagent gas: Methane, flow 1 ml/min |
|---|---|

LC/MS Methods:
Method e:
ZQ Mass Spectrometer from Waters (Single quadrupole mass spectrometer)
Instrument Parameter:
Ionisation method: Electrospray
Polarity: positive ions
Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400
Mass range: 150 to 1000 Da
HP 1100 HPLC from Agilent: solvent degasser, quaternary pump (ZCQ)/binary pump (ZDQ), heated column compartment and diode-array detector.
Column: Phenomenex Gemini C18, 3 ⌊ m, 30×3 mm, Temp: 60° C.
DAD Wavelength range (nm): 200 to 500
Solvent Gradient:
A=water+0.05% HCOOH
B=Acetonitril/Methanol (4:1, v:v)+0.04% HCOOH

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method i:

ZQ Mass Spectrometer from Waters (Single quadrupole mass spectrometer)

Instrument Parameter:
Ionisation method: Electrospray
Polarity: positive or negative ions
Capillary (kV) 3.00, Cone (V) 30.00 V, Extractor (V) 2.00, Source Temperature (° C.) 100, Desolvation Temperature (° C.) 250, Cone Gas Flow (L/Hr) 50, Desolvation Gas Flow (L/Hr) 400
Mass range: 100 to 900 Da HP 1100 HPLC from Agilent: solvent degasser, quaternary pump (ZCQ)/binary pump (ZDQ), heated column compartment and diode-array detector.

Column: Phenomenex Gemini C18, 3 μm, 30×3 mm, Temp: 60° C.
DAD Wavelength range (nm): 200 to 500
Solvent Gradient:
A=water+0.05% HCOOH
B=Acetonitril/Methanol (4:1, v:v)+0.04% HCOOH

| Time | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method k:

SQD Mass Spectrometer from Waters (Single quadrupole mass spectrometer)

Instrument Parameter:
Ionization method: Electrospray
Polarity: positive and negative ions
Capillary: 3.00 kV
Cone: 45.00 V
Extractor: 2.00 V
Source Temperature: 150° C.,
Desolvation Temperature: 250° C.
Cone Gas Flow: 0 L/Hr
Desolvation Gas Flow: 650 L/Hr
Mass range: 100 to 900 Da Acquity UPLC from Waters:

Binary pump, heated column compartment and diode-array detector.

Solvent degasser, binary pump, heated column compartment and diode-array detector.

Column: Phenomenex Gemini C18, 3 μm, 30×2 mm, Temp: 60° C.
DAD Wavelength range (nm): 210 to 500
Solvent Gradient:
A=H2O+5% MeOH+0.05% HCOOH
B=Acetonitril+0.05% HCOOH

| Time | A % | B % | Flow (ml/min) |
|---|---|---|---|
| 0.00 | 100 | 0 | 0.850 |
| 1.2 | 0 | 100.0 | 0.850 |
| 1.50 | 0 | 100.0 | 0.850 |

TABLE A

Table A discloses compounds of formula (I-a) where $R^5$ is methyl, $Y^1$, $Y^2$, $Y^3$ are CH, $G^1$ is oxygen and $R^1$ is hydrogen.

(I-a)

| Compound number | X1 | X2 | X3 | X4 | R2 | LC/MS Method | retention time (min) | observed mass |
|---|---|---|---|---|---|---|---|---|
| A096 | C—Cl | CH | C—Cl | CF3 | thietan-2-ylmethyl- | * | | |
| A097 | C—Cl | CH | C—Cl | CF3 | (1-oxothietan-2-yl)methyl- | e | 1.96 | 519 |
| A098 | C—Cl | CH | C—Cl | CF3 | (1,1-dioxothietan-2-yl)methyl | e | 1.97 | 535 |
| A130 | C—Cl | CH | C—Cl | CF3 | thietan-3-ylmethyl- | * | | |
| A131 | C—Cl | CH | C—Cl | CF3 | 2-(thietan-3-yl)ethanyl | * | | |
| A132 | C—Cl | CH | C—Cl | CF3 | 1,1-Dioxo-thietan-3-ylmethyl | * | | |
| A133 | C—Cl | CH | C—Cl | CF3 | 2-(1,1-dioxothietan-3-yl)ethanyl | * | | |

TABLE A-continued

Table A discloses compounds of formula (I-a) where $R^5$ is methyl, $Y^1, Y^2, Y^3$ are CH, $G^1$ is oxygen and $R^1$ is hydrogen.

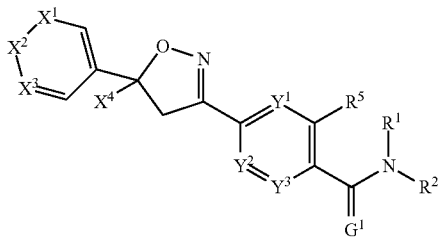

(I-a)

| Compound number | X1 | X2 | X3 | X4 | R2 | LC/MS Method | retention time (min) | observed mass |
|---|---|---|---|---|---|---|---|---|
| A178 | C—Cl | CH | C—Cl | CF3 | 2-(1-oxothietan-3-yl)ethanyl | i | 2.04 | ES+: 533/534 |
| A184 | C—Cl | CH | C—Cl | CF3 | 2-(3-methoxythietan-3-yl)ethyl | i | 2.22 | ES+: 547/549 |
| A192 | C—Cl | CH | C—Cl | CF3 | 1-oxo-thietan-3-ylmethyl- | k | 1.02 | ES−: 519/521 |

*: NMR data as follows: $^1$H-NMR (400 MHz, CDCl$_3$, in ppm)

A096: 2.50 (s, 3H), 2.74 (m, 1H), 3.05 (m, 2H), 3.22 (m, 1H), 3.73 (m, 3H), 4.00 (m, 1H), 4.09 (d, 1H), 6.27 (m, 1H), 7.44 (m, 2H), 7.53 (m, 4H).

A130: 7.55 (m, 4H), 7.50-7.40 (m, 2H), 6.0 (t br, 1H), 4.15-4.10 (d, 1H), 3.75-3.70 (d, 1H), 3.65-3.6 (m, 2H CH2), 3.55-3.5 (m, 1H), 3.40-3.30 (t, 2H), 3.10-3.05 (q, 2H), 2.50 (s, 3H)

A131: 7.55 (m, 4H), 7.50-7.40 (m, 2H), 5.80 (t br, 1H), 4.10 (d, 2H), 3.40 (m, 3H), 3.25 (t, 2H), 3.10 (t, 2H), 2.50 (s, 3H), 1.90 (q, 2H),

A132: 7.55-7.50 (m, 4H), 7.45-7.40 (m, 2H), 6.20 (t br, 1H), 4.30-4.25 (m, 2H), 4.10-4.05 (d, 1H), 4.0-3.9 (m, 2H), 3.75-3.65 (m, 3H), 3.0 (m, 1H), 2.50 (s, 3H)

A133: 7.55-7.50 (m, 4H), 7.45-7.40 (m, 1H), 7.35 (m, 1H), 5.9 (t br, 1H), 4.30-4.25 (m, 2H), 4.10-4.05 (d, 1H), 3.9-3.8 (m, 2H), 3.75-3.65 (d, 1H), 3.5-3.4 (q, 2H), 2.6 (m, 1H), 2.45 (s, 3H), 2.0 (q, 2H).

Table E discloses other compounds.

| Compound number | Compound name | LC/MS Method | retention time (min) | observed mass |
|---|---|---|---|---|
| E3 | 4-[4-(3,5-Dichloro-phenyl)-4-trifluoromethyl-4,5-dihydro-3H-pyrrol-2-yl]-N-(1,1-dioxo-1-thietan-3-ylmethyl)-2-methyl-benzamide | i | 1.94 | 533 |
| E4 | 4-[4-(3,5-Dichloro-phenyl)-4-trifluoromethyl-4,5-dihydro-3H-pyrrol-2-yl]-2-methyl-N-(1-oxo-1-thietan-3-ylmethyl)-benzamide | i | 1.85 | 515 |
| E5 | 4-[4-(3,5-Dichloro-phenyl)-4-trifluoromethyl-4,5-dihydro-3H-pyrrol-2-yl]-2-methyl-N-thietan-3-ylmethyl-benzamide | i | 2.19 | 501 |
| E9 | 2-Methyl-N-thietan-2-ylmethyl-4-[4-(3,4,5-trichloro-phenyl)-4-trifluoromethyl-4,5-dihydro-3H-pyrrol-2-yl]-benzamide | i | 2.14 | 537 |
| E10 | N-(1,1-Dioxo-1-thietan-2-ylmethyl)-2-methyl-4-[4-(3,4,5-trichloro-phenyl)-4-trifluoromethyl-4,5-dihydro-3H-pyrrol-2-yl]-benzamide | i | 2.01 | 569 |
| E11 | 2-Methyl-N-thietan-3-ylmethyl-4-[4-(3,4,5-trichloro-phenyl)-4-trifluoromethyl-4,5-dihydro-3H-pyrrol-2-yl]-benzamide | i | 2.26 | 537 |
| E12 | 2-Methyl-N-(1-oxo-1-thietan-2-ylmethyl)-4-[4-(3,4,5-trichloro-phenyl)-4-trifluoromethyl-4,5-dihydro-3H-pyrrol-2-yl]-benzamide | i | 2.01 | 553 |
| E13 | 2-Methyl-N-(1-oxo-1-thietan-3-ylmethyl)-4-[4-(3,4,5-trichloro-phenyl)-4-trifluoromethyl-4,5-dihydro-3H-pyrrol-2-yl]-benzamide | i | 1.96 | 553 |
| E14 | N-(1,1-Dioxo-1-thietan-3-ylmethyl)-2-methyl-4-[4-(3,4,5-trichloro-phenyl)-4-trifluoromethyl-4,5-dihydro-3H-pyrrol-2-yl]-benzamide | i | 2.03 | 569 |

BIOLOGICAL EXAMPLES

This Example illustrates the insecticidal and acaricidal properties of compounds of formula (I). Tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compounds gave at least 80% control of *Spodoptera littoralis*: A096, A097, A098, A130, A131, A132, A133, A178, A184, A192, E3, E4, E5, E9, E10, E11, E12, E13, E14.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compounds gave at least 80% control of *Heliothis virescens*: A096, A097, A098, A130, A131, A132, A133, A178, A184, A192, E3, E4, E5, E9, E10, E11, E12, E13, E14, H1

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compounds gave at least 80% control of *Plutella xylostella*: A096, A097, A098, A130, A131, A132, A133, A178, A184, A192, E3, E4, E5, E9, E10, E11, E12, E13, E14, H1

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compounds gave at least 80% control of *Diabrotica balteata*: A096, A097, A098, A130, A131, A132, A133, A178, A184, A192, A193, A194, A195, A198, E3, E4, E5, E9, E10, E11, E12, E13, E14, H1

*Thrips tabaci* (Onion *Thrips*):

Sunflower leaf discs were placed on agar in a 24-well microtiter plate and sprayed with test solutions at an application rate of 200 ppm. After drying, the leaf discs were infested with a *thrip* population of mixed ages. After an incubation period of 7 days, samples were checked for mortality.

The following compounds gave at least 80% control of *Thrips tabaci*: A096, A097, A098, A130, A131, A132, A133, A178, A184, A192, E3, E4, E5, E9, E10, E11, E12, E13, E14, H1.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compounds gave at least 80% control of *Tetranychus urticae*: A096, A097, A098, A130, A131, A132, A133, A178, A184, A192, E3, E4, E5, E9, E10, E11, E12, E13, E14, H1.

The invention claimed is:

1. A process for the preparation of a compound of formula IB

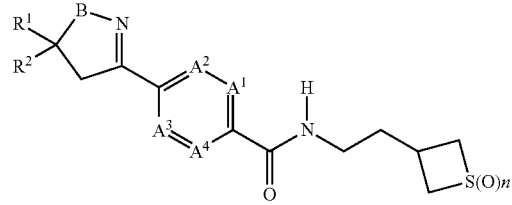

wherein
$A^1$, $A^2$, $A^3$ and $A^4$ are independently of one another C—H, C—$R^3$, or nitrogen;
B is O or $CH_2$;
$R^1$ is $C_1$-$C_8$haloalkyl;
$R^2$ is aryl or aryl substituted by one to five $R^4$, or heteroaryl or heteroaryl substituted by one to five $R^4$;
each $R^3$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, amino, hydroxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, or two $R^3$ on adjacent carbon atoms together form a —CH=CH—CH=CH— bridge or a —N=CH—CH=CH— bridge;
each $R^4$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy, $C_1$-$C_8$haloalkoxy, mercapto, $C_1$-$C_8$alkylthio, $C_1$-$C_8$haloalkylthio, $C_1$-$C_8$alkylsulfinyl, $C_1$-$C_8$haloalkylsulfinyl, $C_1$-$C_8$alkylsulfonyl, $C_1$-$C_8$haloalkylsulfonyl, $C_1$-$C_8$alkylcarbonyl, $C_1$-$C_8$alkoxycarbonyl, aryl or aryl substituted by one to five $R^5$, or heterocyclyl or heterocyclyl substituted by one to five $R^5$;
each $R^5$ is independently halogen, cyano, nitro, $C_1$-$C_4$alkyl, $C_1$-$C_4$haloalkyl, $C_1$-$C_4$alkoxy-, or $C_1$-$C_4$haloalkoxy-;
n is 0, 1 or 2;
comprising
i. reacting a compound of formula VII

with triphenylphosphoranyldiene-acetonitrile or (Cyanomethyl)diethoxyphosphine oxide to give a compound of formula VIII

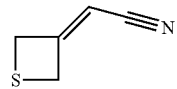

ii. reducing the compound of formula VIII with a suitable reducing agent to give a compound of formula X

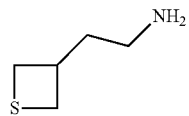
(X)

iii-i. reacting the compound of formula X with a compound of formula V

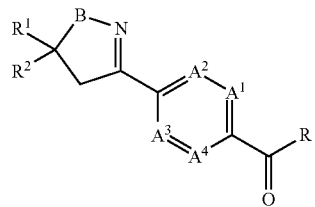
(V)

wherein R is OH, $C_1$-$C_6$alkoxy or Cl, F or Br, and $R^1$, $R^2$, B, $A^1$, $A^2$, $A^3$ and $A^4$ are as defined for compounds of formula IB to give a compound of formula IB; or iii-ii reacting the compound of formula X with a compound of formula VI

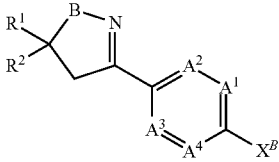
(VI)

wherein $X^B$ is a leaving group, and $R^1$, $R^2$, B, $A^1$, $A^2$, $A^3$ and $A^4$ are as defined for compounds of formula IB with carbon monoxide in the presence of a suitable catalyst to give a compound of formula IB;

and wherein the method optionally comprises oxidizing the sulfur atom of the thietane moiety.

2. The process of claim 1, wherein $X^B$ is a halogen.

3. The process of claim 2, wherein $X^B$ is bromo.

* * * * *